United States Patent [19]
Bennett et al.

[11] Patent Number: 5,885,970
[45] Date of Patent: Mar. 23, 1999

[54] ANTISENSE OLIGONUCLEOTIDES AGAINST HUMAN PROTEIN KINASE C

[75] Inventors: C. Frank Bennett, Carlsbad; Nicholas Dean, Encinitas, both of Calif.

[73] Assignee: ISIS Pharmaceuticals, Inc., Carlsbad, Calif.

[21] Appl. No.: 488,177

[22] Filed: Jun. 7, 1995

Related U.S. Application Data

[63] Continuation-in-part of Ser. No. 89,996, Jul. 9, 1993, Pat. No. 5,703,054, which is a continuation-in-part of Ser. No. 852,852, Mar. 16, 1992, abandoned.

[51] Int. Cl.$^6$ .......................... A61K 48/00; C07H 21/04; C12Q 1/68; C12N 15/85
[52] U.S. Cl. ............................. 514/44; 435/6; 435/91.1; 435/325; 435/354; 435/366; 435/368; 435/371; 435/375; 536/23.1; 536/24.31; 536/24.5
[58] Field of Search ........................... 514/44; 536/23.5, 536/24.1, 24.5, 6, 91.1, 69.1, 172.3, 354, 366, 368, 325, 371, 375; 435/91.1, 91.2, 91.4, 91.41, 91.5, 240.2; 935/2, 5, 6, 8, 10

[56] References Cited

U.S. PATENT DOCUMENTS

| | | | |
|---|---|---|---|
| 4,511,713 | 4/1985 | Miler et al. | 435/6 |
| 4,757,055 | 7/1988 | Miller et al. | 514/44 |
| 4,806,463 | 2/1989 | Goodchild et al. | 435/5 |
| 5,004,810 | 4/1991 | Draper | 536/24.5 |
| 5,034,506 | 7/1991 | Summerton et al. | 528/391 |
| 5,087,617 | 2/1992 | Smith | 514/44 |
| 5,098,890 | 3/1992 | Gerwitz et al. | 514/44 |
| 5,135,917 | 8/1992 | Burch | 514/44 |
| 5,138,045 | 8/1992 | Cook et al. | 536/24.5 |
| 5,166,195 | 11/1992 | Ecker | 514/44 |
| 5,194,428 | 3/1993 | Agrawal et al. | 514/44 |
| 5,264,423 | 11/1993 | Cohen et al. | 514/44 |
| 5,264,618 | 11/1993 | Felgner et al. | 560/224 |
| 5,276,019 | 1/1994 | Cohen et al. | 514/44 |
| 5,286,717 | 2/1994 | Cohen et al. | 514/44 |

FOREIGN PATENT DOCUMENTS

| | | |
|---|---|---|
| WO 93/13121 | 7/1993 | WIPO |
| WO 93/20101 | 10/1993 | WIPO |
| WO 94/29455 | 12/1994 | WIPO |

OTHER PUBLICATIONS

Ono et al. 1988 J. Biol. Chem. 263(14): 6927–6932.
Kawasaki et al. (Jan. 1991), "Synthesis and Biophysical Studies of 2'–dRIBO–2'–F Modified Oligonucleotides" (Conference on Nucleic Acid Therapeutics, Clearwater, FL).
Orkin et al. 7 Dec. 1995 "Report and Recommendations of the Panel to Assess the NIH Investment in Research on Gene Therapy".
Gura, T. 1995 Science 270: 575–577.
Infectious Disease Weekly (23 Oct. 1995), Charles W. Henderson (Publ.).
Boyce et al. 1996 Neurosci. Res. Commun. 18(3): 195–201.
Dean et al. (Mar.) 1995 Proc. Annu. Meet. Assoc. Cancer Res. 36: 413, Abstract 2460.
PR Newswire, 1 Aug. 1996 p. 0801LATH014, (PR Newswire Assoc., Inc.).
Stryer, L. 1975 in: Biochemistry, W.H. Freeman and Company, San Francisco, CA p. 632.
Uhlmann et al. 1990 Chemical Reviews 90(4): 543–584.
Ahmad et al., "Antisense Expression of Protein Kinase Cα Inhibits the Growth and Tumorigenicity of Human Glioblastoma Cells", *Neurosurg.*, 35:904–908 (1994).
Bacher, N. et al., "Isolation and Characterization of PKC–L, A New Member of the Protein Kinase C–Related Gene Family Specifically Expressed in Lung, Skin, and Heart", *Mol. Cell. Biol.* 11:126–133 (1991).
Ballester, R. and Rosen, O., "Fate of Immunoprecipitable Protein Kinase C in $GH_3$ Cells Treated with Phorbol 12–Myristate 13–Acetate", J. Biol. Chem., 260, 260(28):15194–15199 (1985).
Baxter, et al., "PKC–episilon is involved in granuloycte–macrophage colong–stimulating factor signal transduction: Evidence from microphysiometry and antisense oligonucleotide experiments", *Biochemistry*, 31: 10950–10954 (1992).
Berkowitz, P.T. et al., "Synthesis of 1,2–Dihydro–1–(2deoxy–β–D–Erythro–pentafuranosyl)–2–Oxopyrazine 4–oxide, a potent analog of deoxyuridine", *J. Med. Chem.*, 16: 183–184 (1985).
Borek, C. et al., "Long–chain (sphingoid) bases inhibit multistage carcinogenesis in mouse C3H/10T1/2 cells treated with radiation and phorbol 12–myristate 13–acetate", *Proc. Natl. Acad. Sci.*, 88, 1953–1957 (1991).
Brandt, et al., "District Patters of Expression of Different Protein Kinase CmRNA's in Rat Tissues", *Cell.*, 49:57–63 (1987).
Coussens et al., "Multiple, Distinct Form of Bovine and Human Protein Kinase C Suggest Diversity in Cellular Signaling Pathways", *Science*, 233:859–866 (1986).
Endo, et al., "Cell Membrane Signaling as Target in Cancer Therapy: Inhibitory Effect of N,N–Dimethyl and N,N,N,–Trimethyl Sphingosine Derivatives on In Vitro and In Vivo Growth of Human Tumor Cells in Nude Mice", *Cancer Research*, 51:1613–1618 (1991).

(List continued on next page.)

*Primary Examiner*—John L. LeGuyader
*Assistant Examiner*—Mark L. Shibuya
*Attorney, Agent, or Firm*—Woodcock Washburn Kurtz Mackiewicz & Norris, LLP

[57] ABSTRACT

Compositions and methods are provided for the treatment and diagnosis of diseases associated with protein kinase C. Oligonucleotides are provided which are targeted to nucleic acids encoding PKC. Oligonucleotides specifically hybridizable with a translation initiation site, 5'-untranslated region or 3'-untranslated region are provided. Oligonucleotides specifically hybridizable with a particular PKC isozyme or set of isozymes are also provided. Methods of treating animals suffering from disease amenable to therapeutic intervention by modulating protein kinase C expression with an oligonucleotide targeted to PKC are disclosed.

41 Claims, 15 Drawing Sheets

OTHER PUBLICATIONS

Farese, et al., "Antisense DNS downregulates protein kinase C isozymes (beta and alpha) and insulin–stimulated 2–deoxyglucose uptake in rat adipocytes", *Antisense Res. Dev.*, 1 (1): 35–42 (1991).

Finkenzeller, G., "Sequence of Human Protein Kinase C α", *Nucleic Acids Research*, 18:2183 (1990).

Gescher, A. and Dale, I.L., "Protein Kinase C–A Novel Target for Rational Anti–Cancer Drug Design", *Anti–Cancer Drug Design*, 4:93–105 (1989).

Godson, et al., "Inhibition of Expression of Protein Kinase C α by Antisense cDNA Inhibits Phorbol Ester–Mediated Archidonate Release", *The Journal of Biological Chemistry*, 268:11946–11950 (1993).

Hackh's Chemical Dictionary, Grant, et al. (ed.), McGraw–Hill Book Company, New York, p. 312.

Hegemann, L. and G. Mahrle, Pharmacology of the Skin, H. Mukhtar, ed., pp. 357–368, CRC press, Boca Raton, FL, 1992.

Hidaka, H. and Hagiwara, M., "Pharmacology of the isoquinoline sulfonamide protein kinase C inhibitors", *TIPS*, 8:162–164 (1987).

Maister, *Bioworld Today*, Apr. 29, 1994, p. 3.

Kubo, K., et al., "Primary structures of human protein kinase CBI and BII differ only in their C–terminal sequences", *Febs Letters*, 223(1): 138–142 (1987).

Krug, E. et al., "Evidence for increased synthesis as well as increased degradation of protein kinase C after treatment of human ostersarcoma cells with phorbol ester", *J. of Biological Chemistry*, 262(24): 11852–11856 (1987).

Standaert, et al., 1991, J. Cellular Biochem. (Keystone Symposia on Molecular and Cellular Biology, 18–25 Jan.), Suppl. 15B, p.26, abstract CA 211.

Maier, et al., "An oligomer targeted against protein kinase C alpha prevents interleukin–1 alpha induction of cycloxygenase expression in human endothelial cells", *Exp. Cell. Res.*, 205 (1): 52–58 (1993).

Marcus–Sekura, "Techniques for Using Antisense Oligodeoxyribonucleotides to Study Gene Expression", *Analytical Biochemistry*, vol. 172, issued 1988, 289–295.

Nielsen, P.E., et al., "Sequence–Selective Recognition of DNA by Strand Displacement with a Thymine–Substituted Polyamide", *Science*, 254: 1497–1500 (1991).

Nishizuka, Y., "The Molecular Heterogeneity of Protein Kinase C and its Implications for Cellular Regulation", *Nature*, 334: 661–665 (1988).

Osada, S. et al., "A phorbol ester receptor/protein kinase, PKCη, a new member of the protein kinase C family predominantly expressed in lung and skin", *J. of Biological Chemistry*, 265(36): 22434–22440 (1990).

Parker et al., "The complete primary structure of protein kinase c–the major phorbol ester receptor", *Science*, 233:853–866 (1986).

Rothenberg, et al., "Oligodeoxynucleotides as Anti–Sense Inhibitors of Gene Expression: Therapeutic Implications", *J. Natl. Cancer Inst.*, 81(20):1539–1544.

Sakanou, Youichirou et al., "Protein Kinase C Activity as Marker for Colorectal Cancer" *Int. J. Cancer* 48: 803–806 (1991).

Sambrook et al., Molecular Cloning. A Laboratory Manual, Cold Spring Harbor Laboratory Press, 1989, vol. 2, P. 10.59.

Simons et al., "Antisense c–myb oligonucleotides inhibit intimal arterial smooth muscle cell accumulation in vivo", *Nature* 359:67–70 (1992).

1993 Catalog of Products for DNA Research, Glen Research, Sterling, VA, p. 21.

Watson, et al., 1987, in Molecular Biology of The Gene, fourth edition, Benjamin/Cummings Publishing Company, Menlo Park, CA p. 241.

Webster's II New Riverside University Dictionary, Soukhanov, et al., (eds.) 1984, Houghton Mifflin Company, Boston, MA p. 68.

Weinstein, I.B., "Cancer Prevention: Recent Progress and Future Opportunities", *Cancer Research*, 51:5080s–5085s (1991).

Young, S. et al., "Down–regulation of protein kinase C is due to an increased rate of degradation", *Biochem.*, 244:775–779 (1987).

Zon, "Oligonucleotide Analogues as Potential Chemotherapeutic Agents", *Pharmaceuticals Res.*, 5:539–549 (1988).

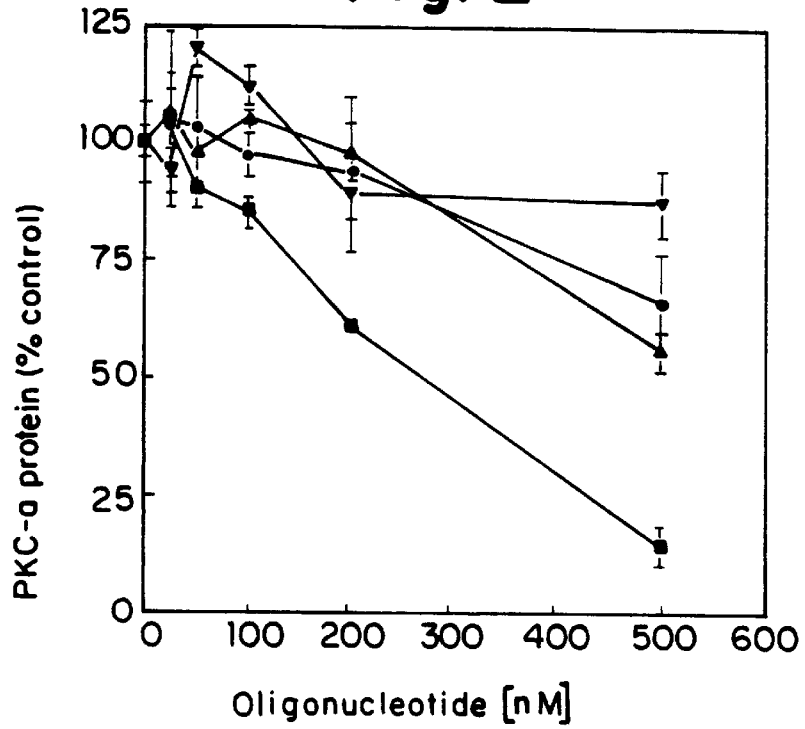
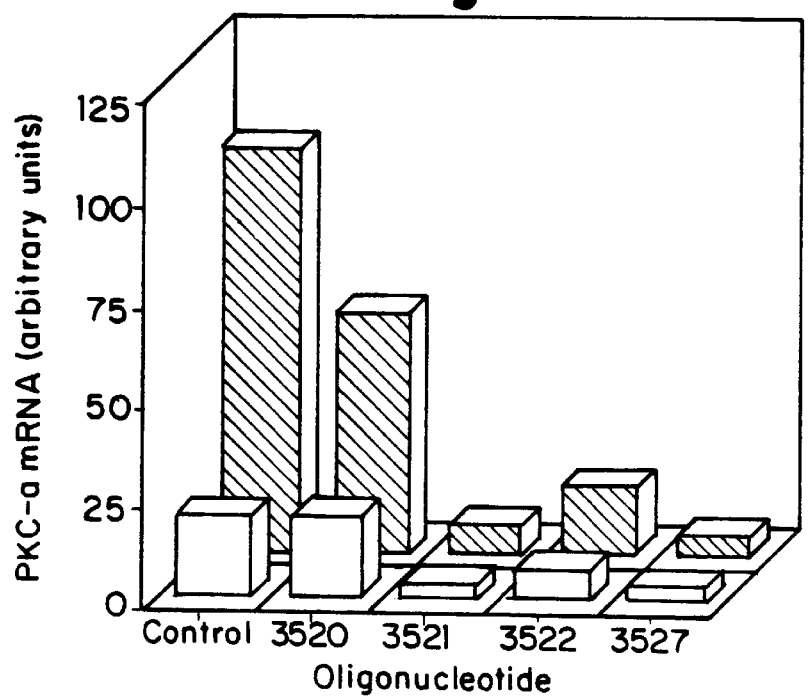

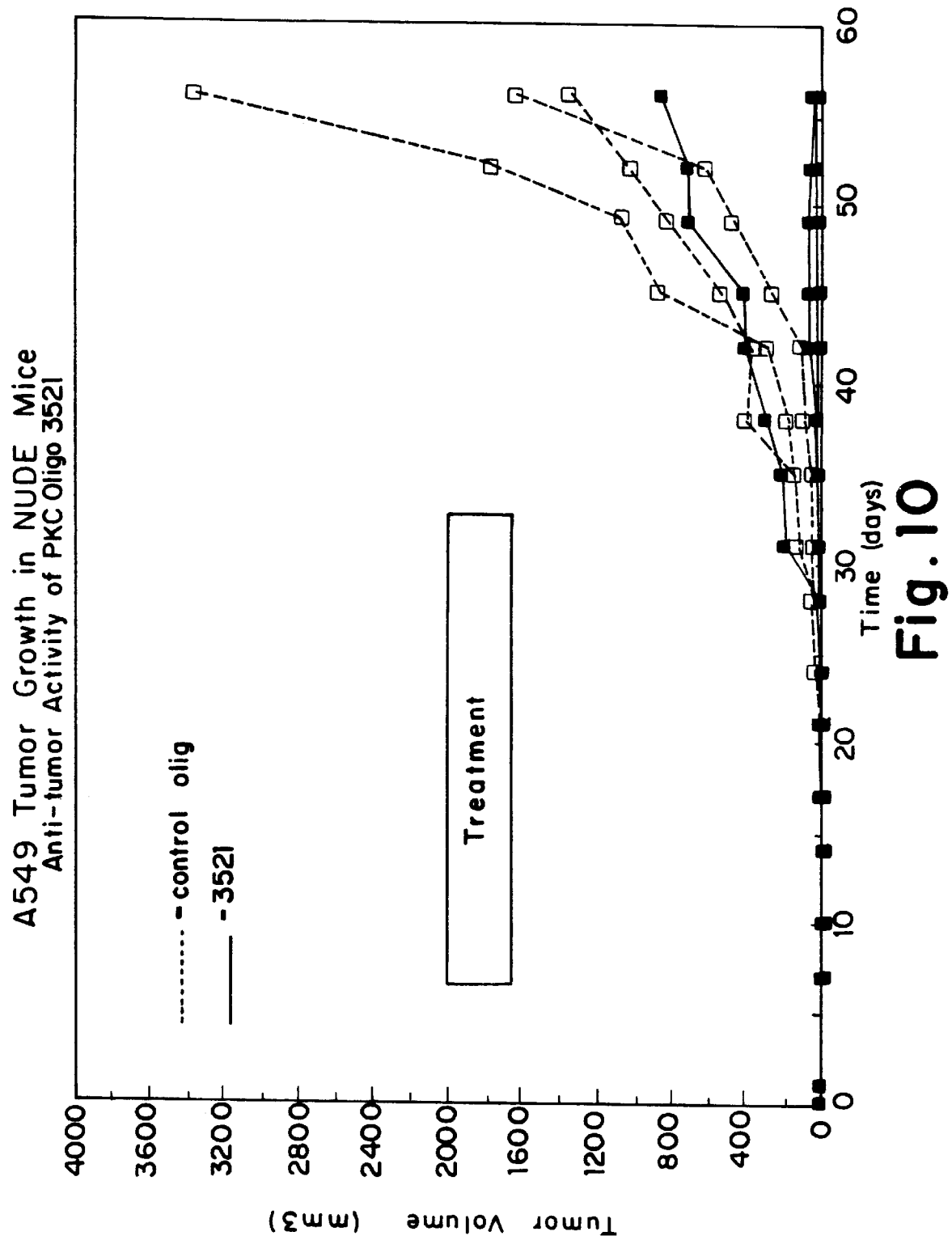

SEQUENCE LISTING ( 1 ) GENERAL INFORMATION:

( i i i ) NUMBER OF SEQUENCES: 121

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

C C C C A A C C A C    C T C T T G C T C C    20

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

G T T C T C G C T G    G T G A G T T T C A    20

( 2 ) INFORMATION FOR SEQ ID NO: 3:

( i ) SEQUENCE CHARACTERISTICS:
        ( A ) LENGTH: 20
        ( B ) TYPE: nucleic acid (C) STRANDEDNESS: single
(D) TOPOLOGY: linear (iv) ANTI-SENSE: yes (xi) SEQUENCE DESCRIPTION: SEQ ID NO: 3:

AAAACGTCAG CCATGGTCCC 20

(2) INFORMATION FOR SEQ ID NO: 4:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 4:

GGATTCACTT CCACTGCGGG 20

(2) INFORMATION FOR SEQ ID NO: 5:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 5:

GAGACCCTGA ACAGTTGATC 20

(2) INFORMATION FOR SEQ ID NO: 6:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 6:

CCCGGGAAAA CGTCAGCCAT 20

(2) INFORMATION FOR SEQ ID NO: 7:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 7:

CTGCCTCAGC GCCCCTTTGC 20

(2) INFORMATION FOR SEQ ID NO: 8:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 8:

AGTCGGTGCA GTGGCTGGAG                                                           20

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 9:

GCAGAGGCTG GGGACATTGA                                                           20

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 10:

GGGCTGGGGA GGTGTTTGTT                                                           20

(2) INFORMATION FOR SEQ ID NO: 11:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 11:

CACTGCGGGG AGGGCTGGGG                                                           20

(2) INFORMATION FOR SEQ ID NO: 12:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 12:

AGCCGTGGCC TTAAAATTTT                                                           20

(2) INFORMATION FOR SEQ ID NO: 13:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 13:

ATTTTCAGGC CTCCATATGG                                                           20

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 14:

AAGAGAGAGA CCCTGAACAG				20

( 2 ) INFORMATION FOR SEQ ID NO: 15:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 15:

GATAATGTTC TTGGTTGTAA				20

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 16:

ATGGGGTGCA CAAACTGGGG				20

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 17:

GTCAGCCATG GTCCCCCCCC				20

( 2 ) INFORMATION FOR SEQ ID NO: 18:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 18:

CGCCGTGGAG TCGTTGCCCG				20

( 2 ) INFORMATION FOR SEQ ID NO: 19:

( i ) SEQUENCE CHARACTERISTICS:
        ( A ) LENGTH: 20
        ( B ) TYPE: nucleic acid (C) STRANDEDNESS: single
(D) TOPOLOGY: linear (iv) ANTI-SENSE: yes (xi) SEQUENCE DESCRIPTION: SEQ ID NO: 19:

TCAAATGGAG GCTGCCCGGC 20

(2) INFORMATION FOR SEQ ID NO: 20:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 20:

TGGAATCAGA CACAAGCCGT 20

(2) INFORMATION FOR SEQ ID NO: 21:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 21:

CATCTTGCGC GCGGGGAGCC 20

(2) INFORMATION FOR SEQ ID NO: 22:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 22:

TGCGCGCGGG GAGCCGGAGC 20

(2) INFORMATION FOR SEQ ID NO: 23:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 23:

CGAGAGGTGC CGGCCCCGGG 20

(2) INFORMATION FOR SEQ ID NO: 24:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 24:

CTCTCCTCGC CCTCCGTCGG                                          20

(2) INFORMATION FOR SEQ ID NO: 25:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 25:

TGGAGTTTGC ATTCACCTAC                                          20

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 26:

AAAGGCCTCT AAGACAAGCT                                          20

(2) INFORMATION FOR SEQ ID NO: 27:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 27:

GCCAGCATGT GCACCGTGAA                                          20

(2) INFORMATION FOR SEQ ID NO: 28:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 28:

ACACCCCAGG CTCAACGATG                                          20

(2) INFORMATION FOR SEQ ID NO: 29:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 29:

CCGAAGCTTA CTCACAATTT                                          20

( 2 ) INFORMATION FOR SEQ ID NO: 30:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 30:

ACTTAGCTCT TGACTTCGGG 20

( 2 ) INFORMATION FOR SEQ ID NO: 31:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 31:

ATGCTGCGGA AAATAAATTG 20

( 2 ) INFORMATION FOR SEQ ID NO: 32:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 32:

ATTTTATTTT GAGCATGTTC 20

( 2 ) INFORMATION FOR SEQ ID NO: 33:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 33:

TTTGGGGATG AGGGTGAGCA 20

( 2 ) INFORMATION FOR SEQ ID NO: 34:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 34:

CCCATTCCCA CAGGCCTGAG 20

( 2 ) INFORMATION FOR SEQ ID NO: 35:

( i ) SEQUENCE CHARACTERISTICS:
        ( A ) LENGTH: 20
        ( B ) TYPE: nucleic acid (C) STRANDEDNESS: single
(D) TOPOLOGY: linear (iv) ANTI-SENSE: yes (xi) SEQUENCE DESCRIPTION: SEQ ID NO: 35:

CGGAGCGCGC CAGGCAGGGA        20

(2) INFORMATION FOR SEQ ID NO: 36:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 36:

CCTTTTCCCA GACCAGCCAT        20

(2) INFORMATION FOR SEQ ID NO: 37:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 37:

GGCCCCAGAA ACGTAGCAGG        20

(2) INFORMATION FOR SEQ ID NO: 38:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 38:

GGATCCTGCC TTTCTTGGGG        20

(2) INFORMATION FOR SEQ ID NO: 39:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 39:

CAGCCATGGC CCCAGAAACG        20

(2) INFORMATION FOR SEQ ID NO: 40:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes ( x i ) SEQUENCE DESCRIPTION: SEQ ID NO: 40:

CGACATGCCG GCGCCGCTGC                                      20

( 2 ) INFORMATION FOR SEQ ID NO: 41:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 41:

CAGACGACAT GCCGGCGCCG                                      20

( 2 ) INFORMATION FOR SEQ ID NO: 42:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 42:

GCCTGCTTCG CAGCGGGAGA                                      20

( 2 ) INFORMATION FOR SEQ ID NO: 43:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 43:

ACAGGTGCAG GAGTCGAGGC                                      20

( 2 ) INFORMATION FOR SEQ ID NO: 44:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 44:

GTCCCGTCTC AGGCCAGCCC                                      20

( 2 ) INFORMATION FOR SEQ ID NO: 45:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 45:

CCTCACCGAT GCGGACCCTC                                      20

( 2 ) INFORMATION FOR SEQ ID NO: 46:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 46:

ATTGAACTTC ATGGTGCCAG        20

( 2 ) INFORMATION FOR SEQ ID NO: 47:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 47:

TCTCACTCCC CATAAGGCTA        20

( 2 ) INFORMATION FOR SEQ ID NO: 48:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 48:

TTCCTTTGGG TTCTCGTGCC        20

( 2 ) INFORMATION FOR SEQ ID NO: 49:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 49:

TTCCATCCTT CGACAGAGTT        20

( 2 ) INFORMATION FOR SEQ ID NO: 50:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 50:

AGGCTGATGC TGGGAAGGTC        20

( 2 ) INFORMATION FOR SEQ ID NO: 51:

( i ) SEQUENCE CHARACTERISTICS:
        ( A ) LENGTH: 20
        ( B ) TYPE: nucleic acid (C) STRANDEDNESS: single
            (D) TOPOLOGY: linear (iv) ANTI-SENSE: yes (xi) SEQUENCE DESCRIPTION: SEQ ID NO: 51:

GTTCTAAGGC TGATGCTGGG                                                                              20

(2) INFORMATION FOR SEQ ID NO: 52:

(i) SEQUENCE CHARACTERISTICS:
            (A) LENGTH: 18
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:52:

TTCTCGCTGG TGAGTTTC                                                                                18

(2) INFORMATION FOR SEQ ID NO: 53:

(i) SEQUENCE CHARACTERISTICS:
            (A) LENGTH: 17
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 53:

TCTCGCTGGT GAGTTTC                                                                                 17

(2) INFORMATION FOR SEQ ID NO: 54:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 54:

AACTCGAGGT GGCCGCCGTC                                                                              20

(2) INFORMATION FOR SEQ ID NO: 55:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 55:

CGCCTTCGCA TAGCCCTTTG                                                                              20

(2) INFORMATION FOR SEQ ID NO: 56:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes ( x i ) SEQUENCE DESCRIPTION: SEQ ID NO: 56:

GGAAGGGGTG ATTGCGGGCC 20

( 2 ) INFORMATION FOR SEQ ID NO: 57:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 57:

AACACGCCCA TTGCCCACCA 20

( 2 ) INFORMATION FOR SEQ ID NO: 58:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 58:

GTCTCAAGAT GGCGTGCTCG 20

( 2 ) INFORMATION FOR SEQ ID NO: 59:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 59:

GCGATGGTTC AGCTGGGCCC 20

( 2 ) INFORMATION FOR SEQ ID NO: 60:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 60:

GCCCTCTCTC TCACTCCCCA 20

( 2 ) INFORMATION FOR SEQ ID NO: 61:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 61:

CTGGGAAGGT CCGATAGAGG 20

( 2 ) INFORMATION FOR SEQ ID NO: 62:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 62:

AAGGCTGATG CTGGGAAGGT     20

( 2 ) INFORMATION FOR SEQ ID NO: 63:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 63:

GCAGGAACGG CGCCATGGTG     20

( 2 ) INFORMATION FOR SEQ ID NO: 64:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 64:

CTGGTTCGCC TCGTCCTCGG     20

( 2 ) INFORMATION FOR SEQ ID NO: 65:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 65:

ATCTGGATGA CGCGCCCCTC     20

( 2 ) INFORMATION FOR SEQ ID NO: 66:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 66:

TTCTTGCAGC GCTCGGCCAG     20

( 2 ) INFORMATION FOR SEQ ID NO: 67:

( i ) SEQUENCE CHARACTERISTICS:
    ( A ) LENGTH: 20
    ( B ) TYPE: nucleic acid (C) STRANDEDNESS: single
(D) TOPOLOGY: linear (iv) ANTI-SENSE: yes (xi) SEQUENCE DESCRIPTION: SEQ ID NO: 67:

TGCAATCCAC GTCCTCCAGG    20

(2) INFORMATION FOR SEQ ID NO: 68:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 68:

GGCTCCGCGG CGGTTCATCG    20

(2) INFORMATION FOR SEQ ID NO: 69:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 69:

AAGCGGTGCG GCATGTCGAT    20

(2) INFORMATION FOR SEQ ID NO: 70:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 70:

GCAGGCTGCC GCAGTGGTCA    20

(2) INFORMATION FOR SEQ ID NO: 71:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 71:

CCTCCCCAGC AACTCCGGTC    20

(2) INFORMATION FOR SEQ ID NO: 72:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (x i) SEQUENCE DESCRIPTION: SEQ ID NO: 72:

AGCGGCCTTT GTCCTGGATG 20

(2) INFORMATION FOR SEQ ID NO: 73:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 73:

GGCCATCCCG GTCCAACAGC 20

(2) INFORMATION FOR SEQ ID NO: 74:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 74:

GGTGCTGGCC CGGCTCTCCC 20

(2) INFORMATION FOR SEQ ID NO: 75:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 75:

GGACCCCGAA AGACCACCAG 20

(2) INFORMATION FOR SEQ ID NO: 76:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 76:

GTGGCTCCAA CCTCCGCTTT 20

(2) INFORMATION FOR SEQ ID NO: 77:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 77:

AGGAGGTGCT CGAATTTGGG 20

( 2 ) INFORMATION FOR SEQ ID NO: 78:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 78:

ACTACCATGG TCGGGGCGGG    20

( 2 ) INFORMATION FOR SEQ ID NO: 79:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 79:

GTCCCACCGC ATGGCGCAGC    20

( 2 ) INFORMATION FOR SEQ ID NO: 80:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 80:

GTTTGGCCGA TGCGCGAGTC    20

( 2 ) INFORMATION FOR SEQ ID NO: 81:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 81:

TGCAGTTGGC CACGAAGTCG    20

( 2 ) INFORMATION FOR SEQ ID NO: 82:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 82:

GTGGGGCATG TTGACGCTGA    20

( 2 ) INFORMATION FOR SEQ ID NO: 83:

( i ) SEQUENCE CHARACTERISTICS:
        ( A ) LENGTH: 20
        ( B ) TYPE: nucleic acid ( C ) STRANDEDNESS: single
( D ) TOPOLOGY: linear ( i v ) ANTI-SENSE: yes ( x i ) SEQUENCE DESCRIPTION: SEQ ID NO: 83:

CCAGAGCAGG GACCCACAGT 20

( 2 ) INFORMATION FOR SEQ ID NO: 84:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 84:

TCTCCTCGGT TGTCAAATGA 20

( 2 ) INFORMATION FOR SEQ ID NO: 85:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 85:

CGGTGCTCCT CTCCTCGGTT 20

( 2 ) INFORMATION FOR SEQ ID NO: 86:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 86:

AGCCAAAATC CTCTTCTCTG 20

( 2 ) INFORMATION FOR SEQ ID NO: 87:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 87:

CATGAGGGCC GATGTGACCT 20

( 2 ) INFORMATION FOR SEQ ID NO: 88:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 88:

ATCCCTTCCT TGCACATCCC 20

( 2 ) INFORMATION FOR SEQ ID NO: 89:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 89:

CCCCAGGGCC CACCAGTCCA 20

( 2 ) INFORMATION FOR SEQ ID NO: 90:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 90:

AGCACCCCCA GGGCCCACCA 20

( 2 ) INFORMATION FOR SEQ ID NO: 91:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 91:

CGTACATCAG CACCCCCAGG 20

( 2 ) INFORMATION FOR SEQ ID NO: 92:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 92:

CCAGCCATCA TCTCGTACAT 20

( 2 ) INFORMATION FOR SEQ ID NO: 93:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 93:

TGCCACACAG CCCAGGCGCA 20

( 2 ) INFORMATION FOR SEQ ID NO: 94:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 94:

TCAGGGCATC AGGTCTTCAC      20

( 2 ) INFORMATION FOR SEQ ID NO: 95:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 95:

CTCTCAGGGC ATCAGGTCTT      20

( 2 ) INFORMATION FOR SEQ ID NO: 96:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 96:

AAGGAAAGTC TGCGGCCGGG      20

( 2 ) INFORMATION FOR SEQ ID NO: 97:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 97:

TGGCGGCTCC CGTTCTGCAG      20

( 2 ) INFORMATION FOR SEQ ID NO: 98:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 98:

GCTTCCTCGG CCGCATGCGT      20

( 2 ) INFORMATION FOR SEQ ID NO: 99:

( i ) SEQUENCE CHARACTERISTICS:
        ( A ) LENGTH: 20
        ( B ) TYPE: nucleic acid ( C ) STRANDEDNESS: single
( D ) TOPOLOGY: linear ( i v ) ANTI-SENSE: yes ( x i ) SEQUENCE DESCRIPTION: SEQ ID NO: 99:

TTGACGCTGA ACCGCTGGGA 20

( 2 ) INFORMATION FOR SEQ ID NO: 100:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 100:

GCCCGGTGCT CCTCTCCTCG 20

( 2 ) INFORMATION FOR SEQ ID NO: 101:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 101:

GGGCCGATGT GACCTCTGCA 20

( 2 ) INFORMATION FOR SEQ ID NO: 102:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 102:

TGGAGGAACA TGAGGGCCGA 20

( 2 ) INFORMATION FOR SEQ ID NO: 103:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 103:

CCCCCAGGGC CCACCAGTCC 20

( 2 ) INFORMATION FOR SEQ ID NO: 104:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 104:

TGCGATGCCA CACAGCCCAG 20

( 2 ) INFORMATION FOR SEQ ID NO: 105:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 105:

TGGGCTCTCA GGGCATCAGG 20

( 2 ) INFORMATION FOR SEQ ID NO: 106:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 106:

CGCCGCTCCC TTCCATCTTG 20

( 2 ) INFORMATION FOR SEQ ID NO: 107:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 107:

CCCCGTAATG CGCCTTGAGG 20

( 2 ) INFORMATION FOR SEQ ID NO: 108:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 108:

CTGTCCACCC ACTTGAGGGT 20

( 2 ) INFORMATION FOR SEQ ID NO: 109:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 109:

TTGGAAGAGG TGGCCGTTGG 20

( 2 ) INFORMATION FOR SEQ ID NO: 110:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 110:

CCTGTTAAAG CGCTTGGCTT                                                                                             20

( 2 ) INFORMATION FOR SEQ ID NO: 111:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 111:

TGCAGGTCAG CGGGACGAGG                                                                                           20

( 2 ) INFORMATION FOR SEQ ID NO: 112:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 112:

AGCCCCTGAG AGATTTTGAT                                                                                           20

( 2 ) INFORMATION FOR SEQ ID NO: 113:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 113:

TTCTTCAACC GCACCAGGAG                                                                                           20

( 2 ) INFORMATION FOR SEQ ID NO: 114:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 114:

TCCTTGCACA TGCCGTAGTC                                                                                           20

( 2 ) INFORMATION FOR SEQ ID NO: 115:

( i ) SEQUENCE CHARACTERISTICS:
        ( A ) LENGTH: 20
        ( B ) TYPE: nucleic acid (C) STRANDEDNESS: single
        (D) TOPOLOGY: linear (iv) ANTI-SENSE: yes (xi) SEQUENCE DESCRIPTION: SEQ ID NO: 115:

GGAGCGCCCG GCCATCATCT 20

(2) INFORMATION FOR SEQ ID NO: 116:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 116:

GGGCTCGCTG GTGAACTGTG 20

(2) INFORMATION FOR SEQ ID NO: 117:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 117:

GACGCACGCG GCCTCACACC 20

(2) INFORMATION FOR SEQ ID NO: 118:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 118:

TCGGAGCCGT GCCCAGCCTG 20

(2) INFORMATION FOR SEQ ID NO: 119:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 119:

CGGGCCAGGT GTGAGGGACT 20

(2) INFORMATION FOR SEQ ID NO: 120:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes -continued (x i) SEQUENCE DESCRIPTION: SEQ ID NO: 120:

CCGCGACGCA GGCACAGCAG                                                    20

(2) INFORMATION FOR SEQ ID NO: 121:

(i) SEQUENCE CHARACTERISTICS:
       (A) LENGTH: 20
       (B) TYPE: nucleic acid
       (C) STRANDEDNESS: single
       (D) TOPOLOGY: linear (i v) ANTI-SENSE: yes (x i) SEQUENCE DESCRIPTION: SEQ ID NO: 121:

GGTCAGTGCA TCGAGTTCTG                                                    20

ANTISENSE OLIGONUCLEOTIDES AGAINST HUMAN PROTEIN KINASE C

CROSS REFERENCE TO RELATED APPLICATIONS

This application is a continuation-in-part of U.S. patent application Ser. No. 08/089,996, filed Jul. 9, 1993, issued on Dec. 30, 1997 as U.S. Pat. 5,703,054, which in turn is a continuation-in-part of U.S. patent application Ser. No. 07/852,852 filed Mar. 16, 1992, now abandoned.

FIELD OF THE INVENTION

This invention relates to therapies, diagnostics, and research reagents for disease states which respond to modulation of the expression of protein kinase C. In particular, this invention relates to antisense oligonucleotides specifically hybridizable with nucleic acids relating to protein kinase C. These oligonucleotides have been found to modulate the expression of protein kinase C.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells [Gescher et al., *Anti-Cancer Drug Design* 4:93–105 (1989)]. Phorbols capable of tumor production can mimic the effect of DAG in activating PKC, suggesting that these tumor promoters act through PKC and that activation of this enzyme is at least partially responsible for the resulting tumorigenesis [Parker et al., *Science* 233:853–866 (1986)].

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer [Weinstein, *Cancer Res.* (*Suppl.*) 51:5080s–5085s (1991)]. It has also been demonstrated that a greater proportion of the PKC in the colonic mucosa of patients with colorectal cancer is in an activated state compared to that of patients without cancer [Sakanoue et al., *Int. J. Cancer* 48:803–806 (1991)].

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo [Endo et al., *Cancer Research* 51:1613–1618 (1991); Borek et al., *Proc. Natl. Acad. Sci.* 88:1953–1957 (1991)]. A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs [Gescher, A. and Dale, I. L., *Anti-Cancer Drug Design,* 4:93–105 (1989)].

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis [Hegemann, L. and G. Mahrle, *Pharmacology of the Skin,* H. Mukhtar, ed., p. 357–368, CRC Press, Boca Raton, Fla., 1992].

The oligonucleotides of the invention are useful in the therapeutic treatment of diseases associated with PKC. Such diseases include hyperproliferative and inflammatory conditions including psoriasis, tumors and cancers, for example glioblastoma, bladder cancer, breast cancer, lung cancer and colon cancer.

PKC is not a single enzyme, but a family of enzymes. At the present time at least seven isoforms (isozymes) of PKC have been identified: isoforms $\alpha$, $\beta$, and $\gamma$ have been purified to homogeneity, and isoforms $\delta$, $\epsilon$, $\zeta$ and $\eta$ have been identified by molecular cloning. These isozymes have distinct patterns of tissue and organ localization (see Nishizuka, *Nature,* 334:661–665 (1988) for review) and may serve different physiological functions. For example, PKC-$\gamma$ seems to be expressed only in the central nervous system. PKC-$\alpha$ and -$\beta$ are expressed in most tissues, but have different patterns of expression in different cell types. For example, both PKC-$\alpha$ and PKC-$\beta$ are expressed in, and have been purified from, human epidermis. While PKC-$\alpha$ has been detected mainly in keratinocytes of the basal layers of the epidermis, PKC-$\beta$ is found mainly in the middle layers of the epidermis and Langerhans cells. PKC-$\eta$ has been found predominantly in the skin and lungs, with levels of expression much higher in these tissues than in the brain. This is in contrast to other members of the PKC family which tend to be most abundantly expressed in the brain [Osada et al., *J. Biol. Chem.* 265:22434–22440 (1990)]. While the PKC isozymes listed here are preferred for targeting by the present invention, other isozymes of PKC are also comprehended by the present invention.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin [Hegemann, L. and G. Mahrle, *Pharmacology of the Skin,* H. Mukhtar, ed., p. 357–368, CRC Press, Boca Raton, Fla., 1992].

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases [Gescher, *Anti-Cancer Drug Design* 4:93–105 (1989)]. Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes. Godson et al. [*J. Biol. Chem.* 268:11946–11950 (1993)] disclosed use of stable transfection of antisense PKC-α cDNA in cytomegalovirus promotor-based expression vectors to specifically decrease expression of PKC-A protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides. Ahmad et al. disclose thar transfection of the human glioblastoma cell line, U-87, with vectors expressing antisense RNA to PKCα inhibits growth of the glioblastoma cells in vitro and in vivo. Ahmad et al., 1994, Neurosurg. 35:904–908. Diaz-Meco Conde et al. disclose a peptide corresponding to the pseudo-substrate region of PKC-ζ and oligonucleotides antisense to this isozyme. WO Application 93/20101. Alvaro et al. have identified a novel mutant form of PKC associated with tumors and disclose oligonucleotide sequences complementary to the mutant form. WO Application 94/29455.

BRIEF DESCRIPTION OF THE DRAWINGS

FIG. 2 is a line graph showing dose-dependent reduction of PKC-α protein levels after oligonucleotide treatment of A549 cells. ▼=ISIS 4632; ■=ISIS 4649; ●=ISIS 4636; ▲=ISIS 4648.

FIG. 3 is a bar graph showing reduction of PKC-α mRNA after treatment of A549 cells with oligonucleotides. Hatched bars represent the 8.5 kb transcript, plain bars represent the 4.0 kb transcript.

FIG. 9 is a set of bar graphs showing the effect of additional oligonucleotides on PKC-α mRNA levels.

FIG. 10 is a line graph showing anti-tumor activity of ISIS 3521. Each dashed line represents tumor volume in one animal treated with control oligonucleotide; each solid line represents tumor volume in one animal treated with ISIS 3521.

FIG. 11 is a set of line graphs showing effect of oligonucleotides on growth of human MDA-MB231 tumors in nude mice.

SUMMARY OF THE INVENTION

Figure 1A:
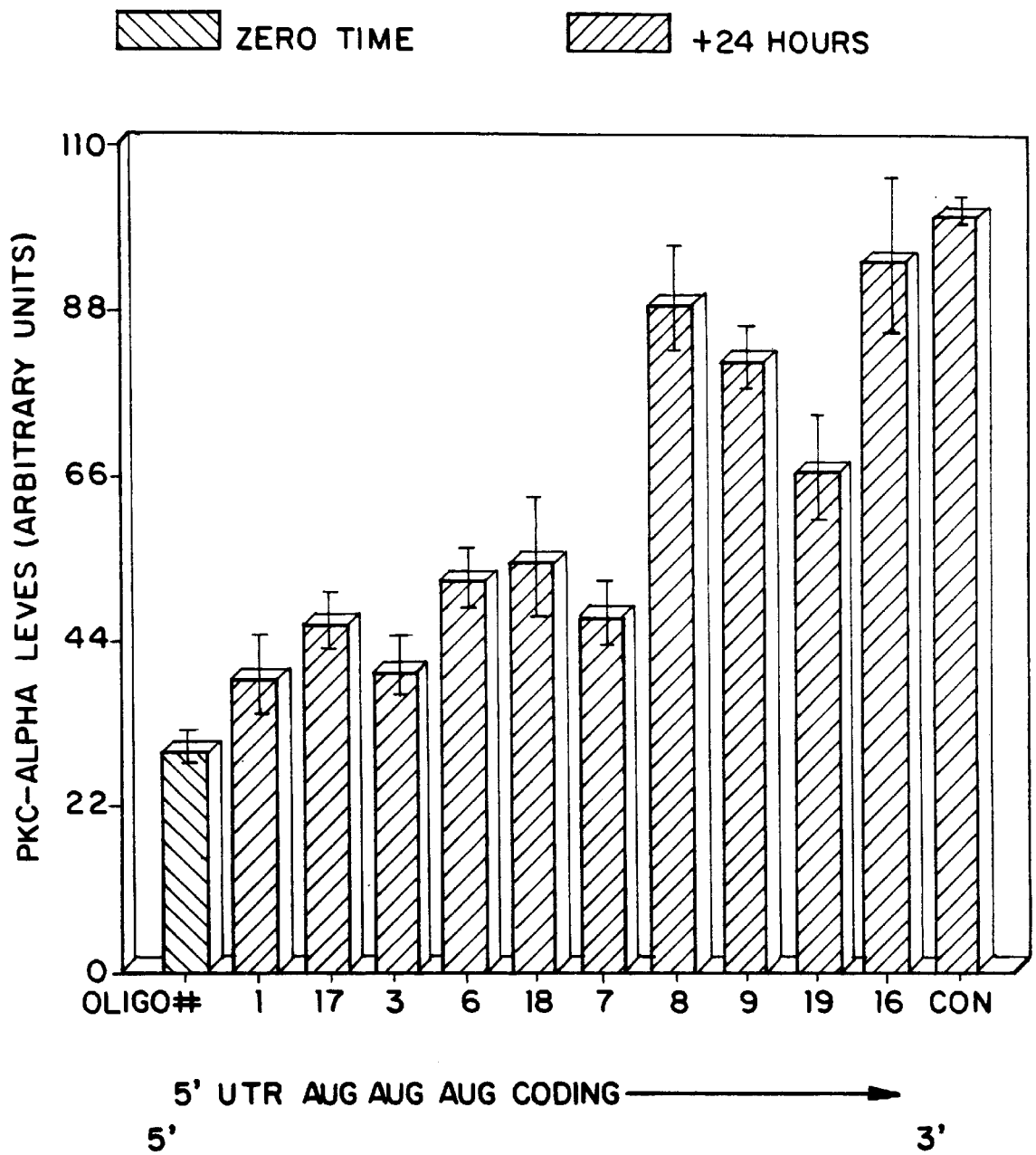
FIG. 1(*a*) and 1(*b*) are graphical depictions of the effects on PKC expression of antisense oligonucleotides hybridizable with PKC-α. Oligonucleotides are arranged by PKC target region, 5' to 3'.

The present invention is directed to methods for treating conditions associated with PKC expression in an animal, especially a human, suspected of having a disease associated with PKC or one of its isozymes. Such methods comprise contacting an animal, or cells, tissues or a bodily fluid of the animal with oligonucleotides that are specifically hybridizable with a nucleic acid that encodes PKC. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

In accordance with the present invention, oligonucleotides are provided that are specifically hybridizable with a nucleic acid that encodes PKC. This relationship is commonly denominated as "antisense". In a preferred embodiment, oligonucleotides are provided that are specifically hybridizable with a nucleic acid encoding a particular PKC isozyme or a particular set of PKC isozymes. Such oligonucleotides may be conveniently and desirably presented in a pharmaceutically acceptable carrier.

In accordance with other preferred embodiments, the oligonucleotides comprise one or more chemical modifications which convey some desired characteristic such as improved target affinity, cellular uptake or stability in the presence of cellular nucleases. Examples of modifications having such utility are 2'-O-alkyl and 2'-fluoro sugar modifications and phosphorothioate backbone modifications.

Other aspects of the invention are directed to modulating the expression of PKC or of a particular PKC isozyme or set of isozymes in an animal or in cells, tissues or bodily fluids of the animal. Such modulation may be used therapeutically or diagnostically. Additional aspects of the invention are directed to methods of detection in cells or tissues of the nucleic acid that encodes PKC and specific detection in cells or tissues of nucleic acid that encodes particular PKC isozymes.

DETAILED DESCRIPTION OF THE INVENTION

Oligonucleotides have been employed as therapeutic moieties for the treatment of disease states in animals and man. For example, workers in the field have now identified antisense, triplex and other oligonucleotide compositions which are capable of modulating expression of genes implicated in viral, fungal and metabolic diseases.

As examples, U.S. Pat. No. 5,135,917, issued Aug. 4, 1992, provides antisense oligonucleotides that inhibit human interleukin-1 receptor expression. U.S. Pat. No. 5,098,890, issued Mar. 24, 1992 in the name of Gewirtz et al., is directed to antisense oligonucleotides complementary to the c-myb oncogene and antisense oligonucleotide therapies for certain cancerous conditions. U.S. Pat. No. 5,087,617, issued Feb. 11, 1992, provides methods for treating cancer patients with antisense oligonucleotides. U.S. Pat. No. 5,166,195 issued Nov. 24, 1992, provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,286,717 (Cohen et al.), issued Feb. 15, 1994, is directed to a mixed linkage oligonucleotide phosphorothioates complementary to an oncogene; U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely administered to humans and clinical trials of several antisense oligonucleotide drugs, targeted both to viral and cellular gene products, are presently underway. The phosphorothioate oligonucleotide, ISIS 2922, has been shown to be effective against cytomegalovirus retinitis in AIDS patients. *BioWorld Today*, Apr. 29, 1994, p. 3. It is thus established that oligonucleotides can be useful therapeutic instrumentalities and can be configured to be useful in treatment regimes for treatment of cells and animal subjects, especially humans.

Current agents which modulate the activity or metabolism of protein kinase C exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In the instant invention, the oligonucleotide is designed to bind directly to mRNA or to a gene, ultimately modulating the amount of PKC protein made from the gene.

This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding PKC; in other words, a PKC gene or mRNA expressed from a PKC gene. The targeting process also includes determination of a site or sites within the nucleic acid sequence for the oligonucleotide interaction to occur such that the desired effect- modulation of gene expression-will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of PKC gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to a polynucleotide formed from naturally occurring nucleobases and pentofuranosyl (sugar) groups joined by native phosphodiester bonds. This term effectively refers to naturally occurring species or synthetic species formed from naturally occurring subunits or their close homologs.

The term "oligonucleotide" may also refer to moieties which function similarly to naturally occurring oligonucleotides but which have non-naturally occurring portions. Thus, oligonucleotides may have altered sugar moieties, nucleobases or inter-sugar ("backbone") linkages. Such modified or substituted oligonucleotides are often preferred over native forms because of properties such as, for example, enhanced cellular uptake, enhanced target binding affinity and increased stability in the presence of nucleases.

Specific examples of some preferred oligonucleotides envisioned for this invention are those which contain intersugar backbone linkages such as phosphotriesters, methyl phosphonates, short chain alkyl or cycloalkyl intersugar linkages or short chain heteroatomic or heterocyclic intersugar linkages. Most preferred are phosphorothioates and those with $CH_2$—NH—O—$CH_2$, $CH_2$—N($CH_3$)—O—$CH_2$ (known as the methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Phosphorothioates are also most preferred. Also preferred are oligonucleotides having morpholino backbone structures. Summerton, J. E. and Weller, D. D., U.S. Pat. No. 5,034,506. In other preferred embodiments, such as the peptide nucleic acid (PNA— referred to by some as "protein nucleic acid") backbone, the phosphodiester backbone of the oligonucleotide may be replaced with a polyamide backbone wherein nucleosidic bases are bound directly or indirectly to aza nitrogen atoms or methylene groups in the polyamide backbone. see, e.g., P. E. Nielsen, M. Egholm, R. H. Berg, O. Buchardt, *Science* 1991, 254, 1497 and U.S. Pat. No. 5,539,082 and incorporated herein by reference. In accordance with other preferred embodiments, the phosphodiester bonds are substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N—alkyl; O—, S—, or N—alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

Chimeric or "gapped" oligonucleotides are also preferred embodiments of the invention. These oligonucleotides contain two or more chemically distinct regions, each comprising at least one nucleotide. Typically, one or more region comprises modified nucleotides that confer one or more beneficial properties, for example, increased nuclease resistance, increased uptake into cells or increased binding affinity for the RNA target. One or more unmodified or differently modified regions retains the ability to direct RNase H cleavage. Chimeric oligonucleotides are disclosed in PCT Publication W093/13121 which is assigned to the assignee of the instant application and which is incorporated by reference herein in its entirety. Examples of chimeric oligonucleotides which are presently preferred are 2'-O-methyl or 2'-O-propyl oligonucleotides having a "deoxy gap" region of 2'-deoxynucleotides. Usually this deoxy gap region is located between the two 2'-alkyl regions. In these preferred embodiments, the internucleotide (backbone) linkages may be uniformly phosphorothioate or some combination of phosphorothioate and phosphodiester linkages.

Affinity of an oligonucleotide for its target (in this case a nucleic acid encoding PKC) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase PKC mRNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PKC gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

All such oligonucleotides are best described as being functionally interchangeable with natural oligonucleotides (or synthesized oligonucleotides along natural lines), but having one or more differences from natural structure. All such oligonucleotides are comprehended by this invention so long as they function effectively to hybridize with the PKC RNA.

The oligonucleotides in accordance with this invention preferably comprise from about 5 to about 50 nucleotide units. As will be appreciated, a nucleotide unit is a base-sugar combination (or a combination of analogous structures) suitably bound to an adjacent nucleotide unit through phosphodiester or other bonds forming a backbone structure.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as phosphorothioates or alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides. Other modified and substituted oligomers can be similarly synthesized.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

The oligonucleotides of this invention are designed to be hybridizable with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

The oligonucleotides of this invention can be used in diagnostics, therapeutics, prophylaxis, and as research reagents and kits. Since the oligonucleotides of this invention hybridize to the PKC gene and its mRNA, sandwich and other assays can easily be constructed to exploit this fact. Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms. Provision of means for detecting hybridization of oligonucleotide with the PKC gene can routinely be accomplished. Such provision may include enzyme conjugation, radiolabelling or any other suitable detection systems. Kits for detecting the presence or absence of PKC may also be prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish PKC-associated tumors, particularly tumors associated with a particular PKC isozyme, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of PKC expression, particularly the specific expression of individual isozymes of PKC. For example, radiolabeled oligonucleotides can be prepared by $^{32}P$ labeling at the 5' end with polynucleotide kinase. Sambrook et al., *Molecular Cloning. A Laboratory Manual*, Cold Spring Harbor Laboratory Press, 1989, Volume 2, p. 10.59. Radiolabeled oligonucleotides are then contacted with tissue or cell samples suspected of PKC expression and the sample is washed to remove unbound oligonucleotide. Radioactivity remaining in the sample indicates bound oligonucleotide (which in turn indicates the presence of PKC) and can be quantitated using a scintillation counter or other routine means. Radiolabeled oligo can also be used to perform autoradiography of tissues to determine the localization, distribution and quantitation of PKC expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits PKC expression to be detected.

Analogous assays for fluorescent detection of PKC expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21).

Each of these assay formats is known in the art. One of skill could easily adapt these known assays for detection of raf expression in accordance with the teachings of the invention providing a novel and useful means to detect PKC expression, particularly of specific PKC isozymes.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or by intravenous, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates. Optimum dosages may vary depending on the relative potency of individual oligonucleotides, and can generally be calculated based on IC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is psoriasis, a reduction or ablation of the skin plaque is an indication that the administered dose has a therapeutic effect. Similarly, in mammals being treated for cancer, therapeutic effects are assessed by measuring the rate of growth or the size of the tumor, or by measuring the production of compounds such as cytokines, which production is an indication of the progress or regression of the tumor.

The following examples illustrate the present invention and are not intended to limit the same.

EXAMPLES

Example 1

Oligonucleotide synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems n(Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-0-methyl phosphorothioate oligonucleotides were synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl phosphorothioate oligonucleotides may be prepared by slight modifications of this procedure.

2'-fluoro phosphorothioate oligonucleotides were synthesized using 5'-dimethoxytrityl-3'-phosphoramidites and prepared as described in Example 25. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, Ph 7.0.

The oligonucleotides tested are presented in Table 1. Sequence data are from the CDNA sequence published by Finkenzeller et al., *Nucl. Acids Res.* 18:2183 (1990); Genbank accession number X52479. The sequence numbers given under the oligonucleotides are relative to the first residue to be sequenced on the CDNA, which is 28 residues upstream of the ATG start codon.

TABLE 1

OLIGONUCLEOTIDES TARGETED TO HUMAN PKC-α

| SEQ ID | Sequence | Target | ISIS # |
|---|---|---|---|
| 1 | CCC CAA CCA CCT CTT GCT CC<br>19                     1 | 5'<br>Untranslated | 3520 |
| 2 | GTT CTC GCT GGT GAG TTT CA<br>2063                  2044 | 3'<br>Untranslated | 3521 |
| 3 | AAA ACG TCA GCC ATG GTC CC<br>41                   22 | Translation<br>init. codon | 3522 |
| 4 | GGA TTC ACT TCC ACT GCG GG<br>2109                 2090 | 3'<br>Untranslated | 3526 |
| 5 | GAG ACC CTG AAC AGT TGA TC<br>2211                 2192 | 3'<br>Untranslated | 3527 |
| 6 | CCC GGG AAA ACG TCA GCC AT<br>47                  28 | Translation<br>init codon | 3674 |
| 7 | CTG CCT CAG CGC CCC TTT GC<br>110                   91 | Internal<br>(C1) domain | 3682 |
| 8 | AGT CGG TGC AGT GGC TGG AG<br>193                  174 | Internal<br>(C1) domain | 3686 |
| 9 | GCA GAG GCT GGG GAC ATT GA<br>480                  461 | Internal<br>(C1) domain | 3687 |
| 10 | GGG CTG GGG AGG TGT TTG TT<br>2080                 2061 | 3'<br>Untranslated | 3695 |
| 11 | CAC TGC GGG GAG GGC TGG GG<br>2098                 2079 | 3'<br>Untranslated | 3875 |
| 12 | AGC CGT GGC CTT AAA ATT TT<br>2137                 2118 | 3'<br>Untranslated | 3878 |
| 13 | ATT TTC AGG CCT CCA TAT GG<br>2168                 2149 | 3'<br>Untranslated | 3879 |
| 14 | AAG AGA GAG ACC CTG AAC AG<br>2217                 2198 | 3'<br>Untranslated | 3884 |
| 15 | GAT AAT GTT CTT GGT TGT AA<br>2235                 2216 | 3'<br>Untranslated | 3885 |
| 16 | ATG GGG TGC ACA AAC TGG GG<br>2027                 2008 | Internal<br>(C3) domain | 3886 |
| 17 | GTC AGC CAT GGT CCC CCC CC<br>36                   17 | Translation<br>init. codon | 3890 |
| 18 | CGC CGT GGA GTC GTT GCC CG<br>63                   44 | Internal<br>(V1) domain | 3891 |
| 19 | TCA AAT GGA GGC TGC CCG GC<br>1643                 1624 | Internal<br>(C3) domain | 3892 |
| 20 | TGG AAT CAG ACA CAA GCC GT<br>2151                 2132 | 3'<br>Untranslated | 3947 |

Example 2

Cell culture and treatment with phorbol esters and oligonucleotides targeted to PKC-α

PKC protein half-lives have been reported to vary from 6.7 hours to over 24 hours [Young et al., *Biochem. J.* 244:775–779 (1987); Ballester et al., *J. Biol. Chem.* 260:15194–15199 (1985)]. These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., [Krug et al., *J. Biol. Chem.* 262:11852–11856 (1987)] lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 109 fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 μM DOTMA (Lipofectin reagent, BRL, Bethesda, Md.) was added. Oligonucleotides were added to a concentration of 1 μM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 μM) were added and the cells were incubated at 37° C. for 24 hours.

Cells were washed three times in phosphate-buffered saline (PBS) and cellular proteins were extracted in 120 μl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 3
Immunoblot assay for PKC expression

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-β (UBI, Lake Placid N.Y.) diluted to 0.2 μg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). PKC-β appears as a single band with a molecular weight of 80 kD.

Figure 1B:
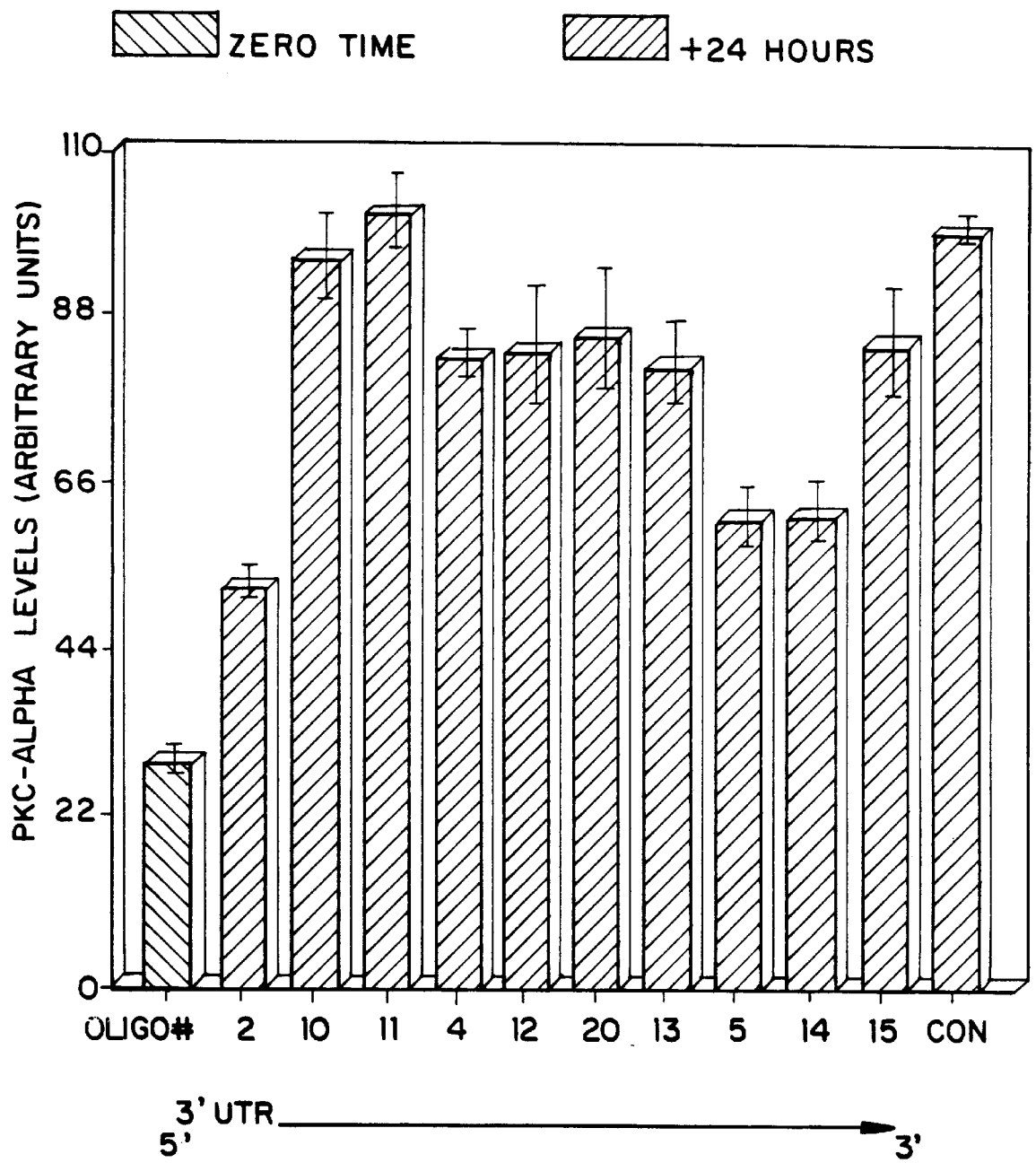

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (Sequence Nos. 1, 3, 17, 7, 6). The next most effective oligonucleotides are targeted toward the 3' untranslated region of the RNA (oligos 2, 5, 14).

Example 4
Other isozymes of PKC

Results with oligonucleotides targeting human PKC-α demonstrated that the most effective target sequences were those surrounding the translation initiation codon and the 3' untranslated region. It is believed that these sequences will also be effective targets for oligonucleotides directed against other isozymes of PKC. The other isozymes of human PKC for which sequence data are available are PKC-β (types I and II), PKC-γ (partial sequence) and PKC-η. Antisense oligonucleotides which are likely to be effective inhibitors of PKC are identified below. These oligonucleotides are synthesized as in Example 1, and can be screened as in Examples 2 and 3, using appropriate antibodies where available. Alternatively, a reporter gene assay system can be established, transiently co-expressing the desired isozyme of PKC with luciferase under the influence of the TPA-responsive enhancer or other suitable promoter. PKC expression is then assayed by measuring luciferase activity using standard procedures. Luciferase is extracted from cells by lysis with the detergent Triton X-100, as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y. (1987). A Dynatech ML1000 luminometer is used to measure peak luminescence upon addition of luciferin (Sigma) to 625 μM.

PKC-β, types I and II

Sequence data are from Kubo et al., *FEBS Lett.* 223:138–142 (1987); Genbank accession numbers X06318, M27545, X07109. Sequences are numbered from the first 5' base sequenced on the cDNA. PKC-β types I and II are the result of alternative mRNA splicing of a single gene product. This results in proteins with identical amino termini (5' end of the mRNA); however, there is sequence divergence in the carboxy termini (3' end of the mRNA). The following oligonucleotides, targeted to the translation initiation codon, are expected to modulate expression of both PKC-β types I and II:

TABLE 2

OLIGONUCLEOTIDES TARGETED TO PKC-β TYPES I AND II

| SEQ ID | Sequence | Target |
|---|---|---|
| 21 | CAT CTT GCG CGC GGG GAG CC<br>139                       120 | Translation init. |
| 22 | TGC GCG CGG GGA GCC GGA GC<br>134                       115 | Translation init. |
| 23 | CGA GAG GTG CCG GCC CCG GG<br>113                       94 | Translation init. |
| 24 | CTC TCC TCG CCC TCG CTC GG<br>183                       164 | Translation init. |

The following antisense oligonucleotides are targeted to the 3'-untranslated region of PKC-β type I:

TABLE 3

OLIGONUCLEOTIDES TARGETED TO PKC-β TYPE I

| SEQ ID | Sequence | Target |
|---|---|---|
| 25 | TGG AGT TTG CAT TCA CCT AC<br>2168                      2149 | 3' Untranslated |
| 26 | AAA GGC CTC TAA GAC AAG CT<br>2285                      2266 | 3' Untranslated |
| 27 | GCC AGC ATG TGC ACC GTG AA<br>2250                      2231 | 3' Untranslated |
| 28 | ACA CCC CAG GCT CAA CGA TG<br>2186                      2167 | 3' Untranslated |
| 29 | CCG AAG CTT ACT CAC AAT TT<br>2569                      2550 | 3' Untranslated |

The following antisense oligonucleotides are targeted to the 3'-untranslated region of PKC-β Type II:

TABLE 4

OLIGONUCLEOTIDES TARGETED TO PKC-β TYPE II

| SEQ.ID | Sequence | Target |
|---|---|---|
| 30 | ACT TAG CTC TTG ACT TCG GG<br>2160                      2141 | 3' Untranslated |
| 31 | ATG CTG CGG AAA ATA AAT TG<br>2420                      2401 | 3' Untranslated |
| 32 | ATT TTA TTT TGA GCA TGT TC<br>2663                      2644 | 3' Untranslated |
| 33 | TTT GGG GAT GAG GGT GAG CA<br>2843                      2824 | 3' Untranslated |
| 34 | CCC ATT CCC ACA GGC CTG AG<br>3137                      3118 | 3' Untranslated |

PKC-γ

Sequence data are from Coussens et al., *Science* 233:859–866 (1986); Genbank accession number M13977. Sequences are numbered from the first 5' base sequenced in the cDNA. The full sequence is not available: the extreme 3' end of the open reading frame and the 3' untranslated region are missing. Consequently these regions are not presently available as antisense targets.

TABLE 5

OLIGONUCLEOTIDES TARGETED TO PKC-λ

| SEQ.ID | Sequence | Target |
|---|---|---|
| 35 | CGG AGC GCG CCA GGC AGG GA<br>51                          32 | 5' Untranslated |
| 36 | CCT TTT CCC AGA CCA GCC AT<br>215                        196 | Translation init. |
| 37 | GGC CCC AGA AAC GTA GCA GG<br>195                        176 | 5' of start codon |
| 38 | GGA TCC TGC CTT TCT TGG GG<br>170                        151 | 5' Untranslated |
| 39 | CAG CCA TGG CCC CAG AAA CG<br>202                        183 | Translatian init. |

PKC-η

Sequence data for PKC-η are from Bacher and colleagues [Bacher et al., *Mol. Cell. Biol.* 11:126–133 (1991)]; Genbank accession number M55284. They assign their isozyme the name PKC-L; however the sequence is almost identical to that of mouse PKC-η, so the latter nomenclature is used here for consistency. Sequences are numbered from the first 5' base sequenced in the cDNA.

TABLE 6

OLIGONUCLEOTIDES TARGETED TO PKC-η

| SEQ.ID | Sequence | Target |
|---|---|---|
| 40 | CGA CAT GCC GGC GCC GCT GC<br>172                        153 | Translation init. |
| 41 | CAG ACG ACA TGC CGG CGC CG<br>176                        157 | Translation init. |
| 42 | GCC TGC TTC GCA GCG GGA GA<br>138                        119 | Translation init. |
| 43 | ACA GGT GCA GGA GTC GAG GC<br>86                          67 | Translation init. |
| 44 | GTC CCG TCT CAG GCC AGC CC<br>111                         92 | Translation init. |
| 45 | CCT CAC CGA TGC GGA CCC TC<br>221                        202 | Translation init. |
| 46 | ATT GAA CTT CAT GGT GCC AG<br>193                        174 | Translation init. |
| 47 | TCT CAC TCC CCA TAA GGC TA<br>2046                      2027 | 3' Untranslated |
| 48 | TTC CTT TGG GTT CTC GTG CC<br>2067                      2048 | 3' Untranslated |
| 49 | TTC CAT CCT TCG ACA GAG TT<br>2353                      2336 | 3' Untranslated |
| 50 | AGG CTG ATG CTG GGA AGG TC<br>2300                      2281 | 3' Untranslated |
| 51 | GTT CTA AGG CTG ATG CTG GG<br>2306                      2287 | 3' Untranslated |

Example 5

Dose response of phosphorothioate/2'-O-methyl oligonucleotide effects on PKC-α protein synthesis A series of phosphorothioate, fully 2'-O-methyl oligonucleotides having SEQ ID NO: 1, 2, 3 and 5 were synthesized. A549 cells were treated with 500 nM PDBu for 18 hours to downregulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described in Example 3. Results were quantified with a phosphorimager (Molecular Dynamics, Sunnyvale Calif.) and are shown in FIG. 2 expressed as percent of control (saline treatment). ISIS 4649 (SEQ ID NO: 3; squares) reduced PKC-α protein levels by 85–90% at 500 nM and had an IC50 of approximately 260 nM.

Example 6

Effect of antisense oligonucleotides on PKC-α mRNA levels

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). Results are shown in FIG. 3. Oligonucleotides 3521 (SEQ ID NO: 2), 3522 (SEQ ID NO: 3) and 3527 (SEQ ID NO: 5) gave better than 50% reduction of PKC-α mRNA levels. Oligonucleotides 3521 and 3527 gave approximately 80% reduction of the smaller transcript and over 90% reduction of the larger transcript.

Example 7
Chimeric (deoxy gapped) 2'-O-methyl oligonucleotides

Figure 4:
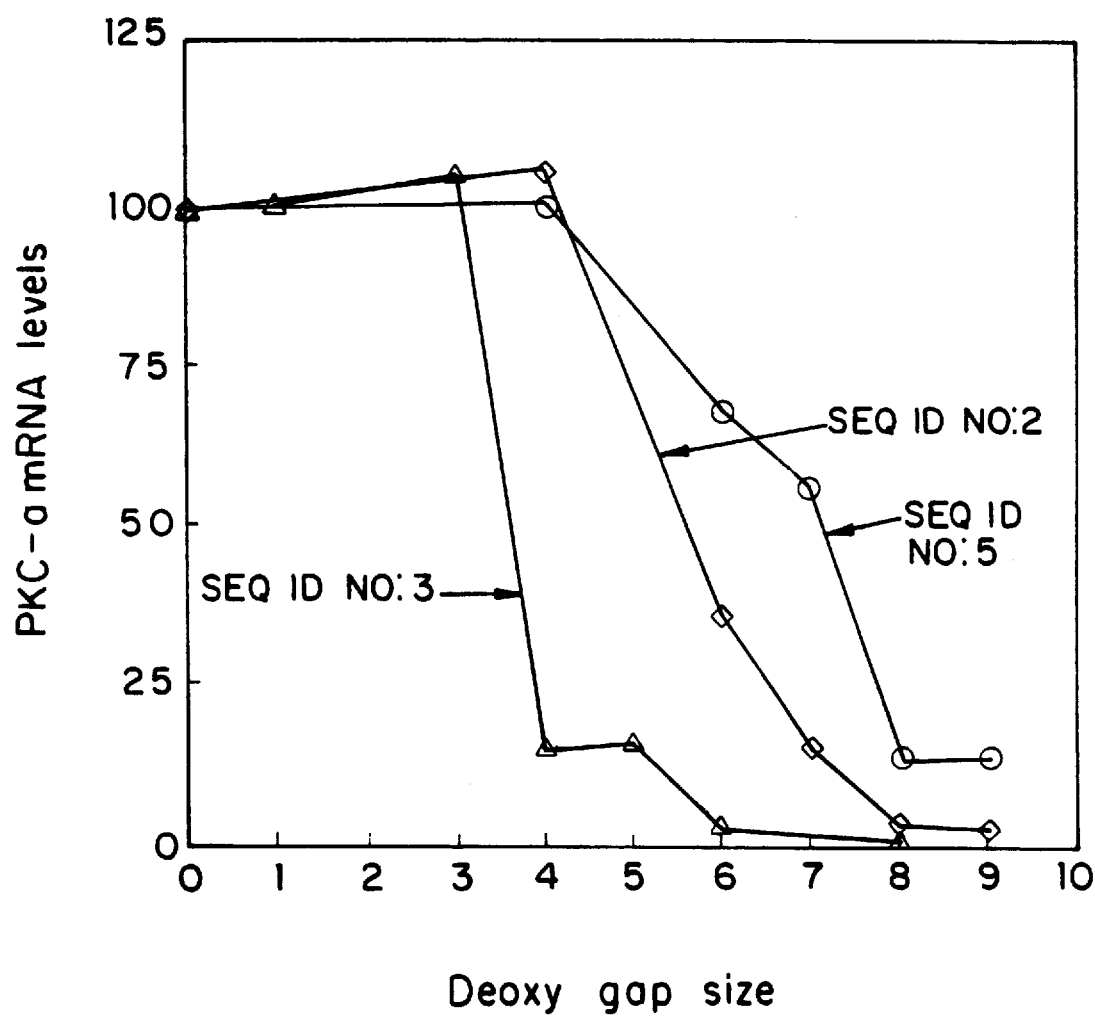
FIG. 4 is a line graph showing the relationship between deoxy gap length and activity of chimeric oligonucleotides against PKC.

Oligonucleotides 3521 (SEQ ID NO: 2), 3522 (SEQ ID NO: 3) and 3527 (SEQ ID NO: 5) were chosen for further study and modification. Oligonucleotides having these sequences were synthesized as uniformly phosphorothioate chimeric oligonucleotides having a centered deoxy gap of various lengths flanked by 2'-O-methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligonucleotide having SEQ ID NO: 3 reduced PKC-α mRNA by approximately 83% with a deoxy gap length of four nucleotides, and gave nearly complete reduction of PKC-α mRNA with a deoxy gap length of six or more.

Figure 5:
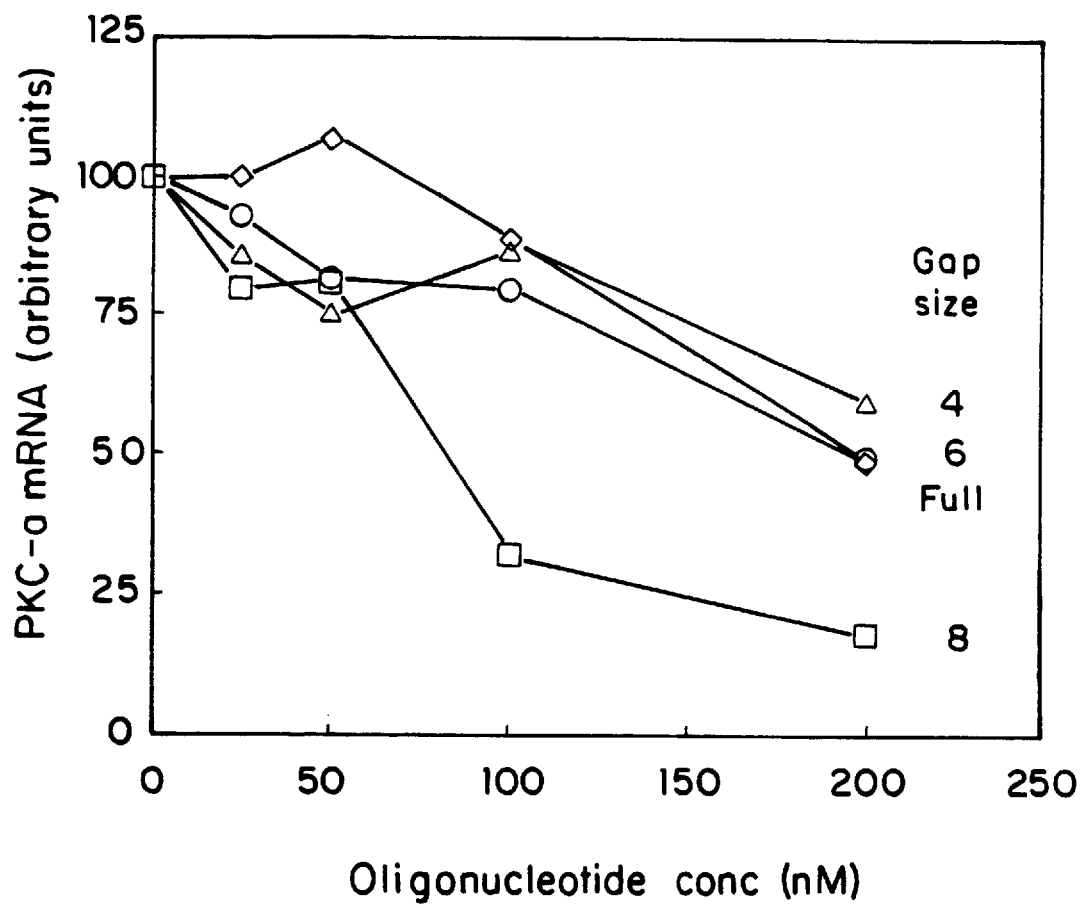
FIG. 5 is a line graph showing dose response curves for chimeric oligonucleotides (all SEQ ID NO: 3) with different deoxy gap lengths.

Dose-response curves for these oligonucleotides are shown in FIG. 5. The 2'-O-methyl chimeric oligonucleotides with four- or six-nucleotide deoxy gaps have an IC50 for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an IC50 of approximately 85 nM.

Several variations of this chimeric oligonucleotide (SEQ. ID NO: 3) were compared for ability to lower PKC-α mRNA levels. These oligonucleotides are shown in Table 7.

TABLE 7

Chimeric 2'-O-methyl/deoxy P = S oligonuclectides
bold = 2'-O-methyl; s = P = S linkage, o = P = O linkage

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5352 | AsAsAsAsCsGsTsCsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCsAsTsGoGoToCoCsC | 3 |
| 7024 | AsAoAoAoCoGsToCsAoGsCoCsAsTsGoGoToCoCsC | 3 |

Figure 6:
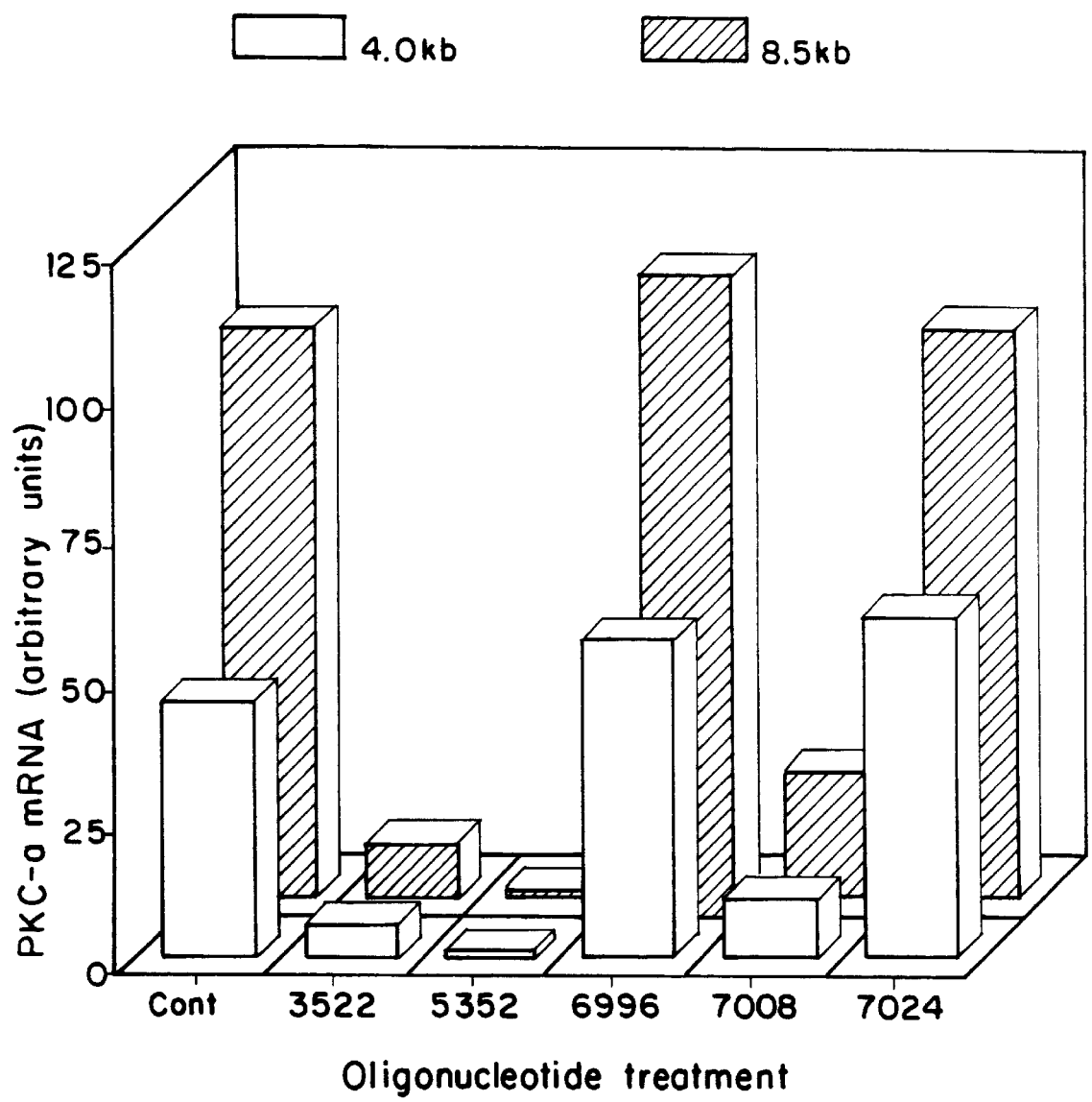
FIG. 6 is a bar graph showing the effects of several 2'-O-methyl chimeric oligonucleotides of SEQ ID NO: 3 on PKC-α mRNA levels. Hatched bars represent the 8.5 kb transcript, plain bars represent the 4.0 kb transcript.

Effects of these oligonucleotides on PKC-α mRNA levels is shown in FIG. 6. Oligonucleotides 7008, 3522 and 5352 show reduction of PKC-α mRNA, with 5352 being most active.

A series of 2'-O-propyl chimeric oligonucleotides was synthesized having SEQ ID NO: 3. These oligonucleotides are shown in Table 8.

TABLE 8

Chimeric 2'-O-propyl/deoxy P = S oligonucleotides
bold = 2'-C-propyl; s = P = S linkage, o = P = O linkage

| OLIGO # | SEQUENCE | SEQ ID NO: |
|---|---|---|
| 7199 | AsAsAsAsCsGsTsCsAsGsCsCsAsTsGsGsTsCsCsC | 3 |
| 7273 | AoAoAoAoCoGsTsCsAsGsCsCsAsTsGoGoToCoCoC | 3 |
| 7294 | AsAoAoAoCoGsTsCsAsGsCsCsAsTsGoGoToCoCsC | 3 |
| 7295 | AsAoAoAoCoGsToCsAoGsCoCsAsTsGoGoToCoCsC | 3 |

These 2'-O-propyl chimeric oligonucleotides were compared to the 2'-O-methyl chimeric oligonucleotides.

Figure 7:
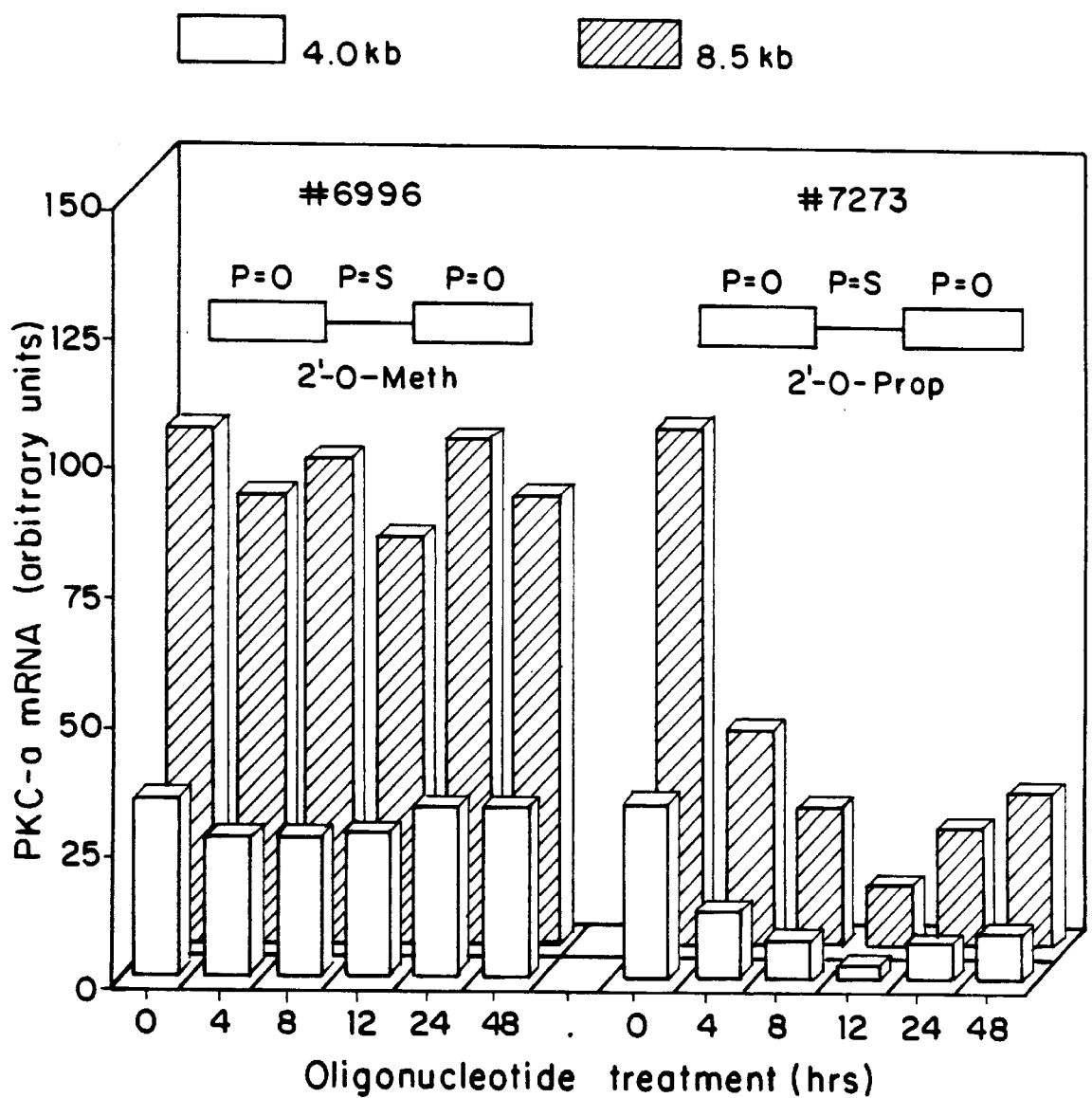
FIG. 7 is a bar graph and diagram showing the effects of several 2'-O-methyl and 2'-O-propyl chimeric oligonucleotides (6996, 7273) of SEQ ID NO: 3 on PKC-α mRNA levels. Hatched bars represent the 8.5 kb transcript, plain bars represent the 4.0 kb transcript.
Figure 8:
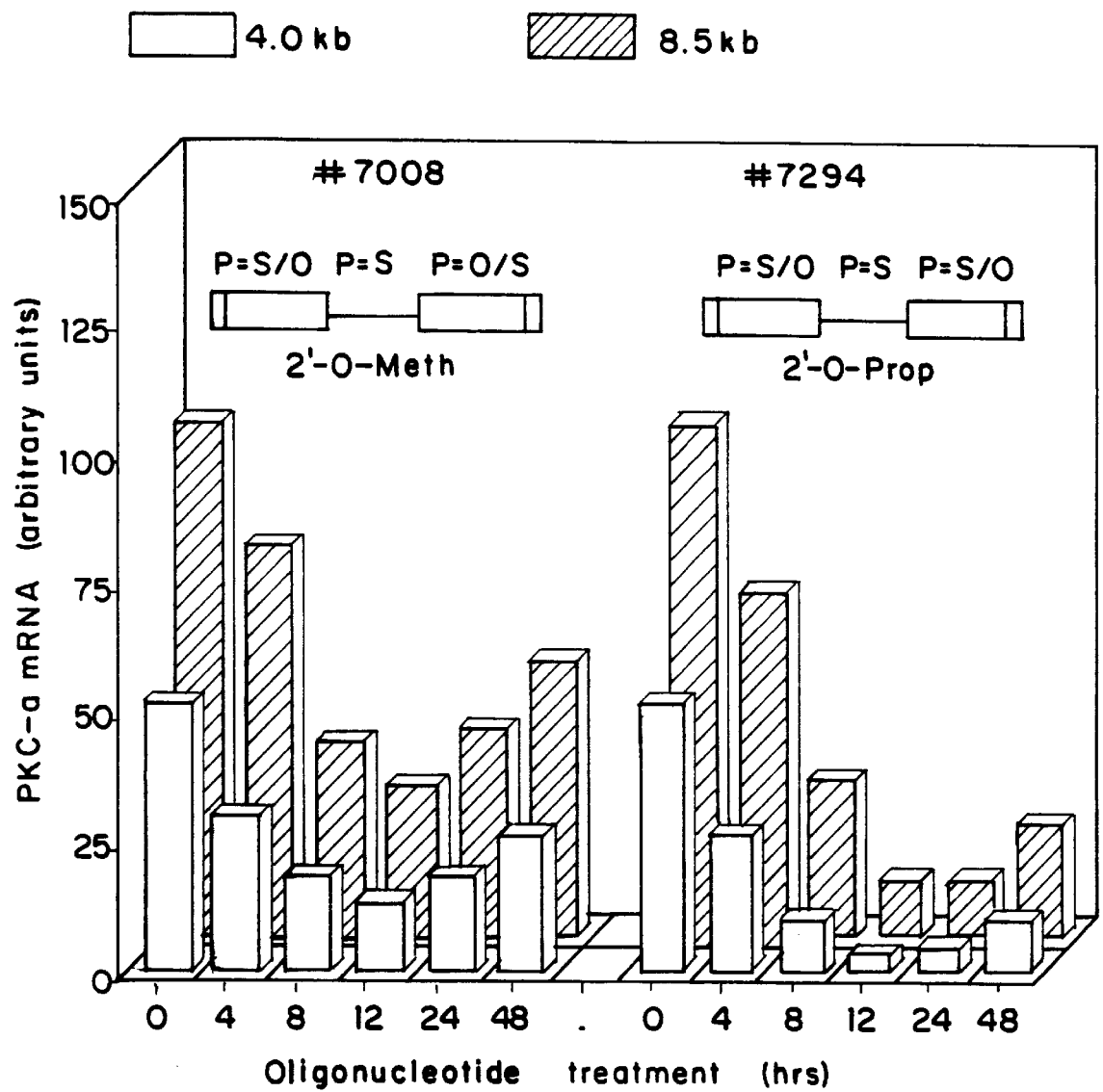
FIG. 8 is a bar graph and diagram showing the effects of additional 2'-O-methyl and 2'-O-propyl chimeric oligonucleotides (7008, 7294) of SEQ ID NO: 3 on PKC-α mRNA levels. Hatched bars represent the 8.5 kb transcript, plain bars represent the 4.0 kb transcript.

Oligonucleotides 7273 and 7294 were more active than their 2'-O-methyl counterparts at lowering PKC-α mRNA levels. This is shown in FIGS. 7 and 8.

Example 8
Additional oligonucleotides which decrease PKC-α mRNA

Additional phosphorothioate oligonucleotides targeted to the human PKC-α 3' untranslated region were designed and synthesized. These sequences are shown in Table 9.

TABLE 9

Chimeric 2'-O-propyl/deoxy P = S oligonucleotides
targeted to PKC-α 3'-UTR
bold = 2'-O-propyl; s = P = S linkage, o = P = O linkage

| OLIGO # | SEQUENCE | SEQ ID NO: |
|---|---|---|
| 6632 | TsTsCs TsCsGs CsTsGs GsTsGs AsGsTs TsTsC | 52 |
| 6653 | TsTsCs TsCsGs CsTsGs GsTsGs AsGsTs TsTsC | 52 |
| 6665 | ToToCo TsCsGs CsTsGs GsTsGs AsGsTo ToToC | 52 |
| 7082 | TsCsTs CsGsCs TsGsGs TsGsAs GsTsTs TsC | 53 |
| 7083 | TsCsTs CsGsCs TsGsGs TsGsAs GsTsTs TsC | 53 |
| 7084 | ToCoTo CsGsCs TsGsGs TsGsAs GsToTo ToC | 53 |

Figure 9A:
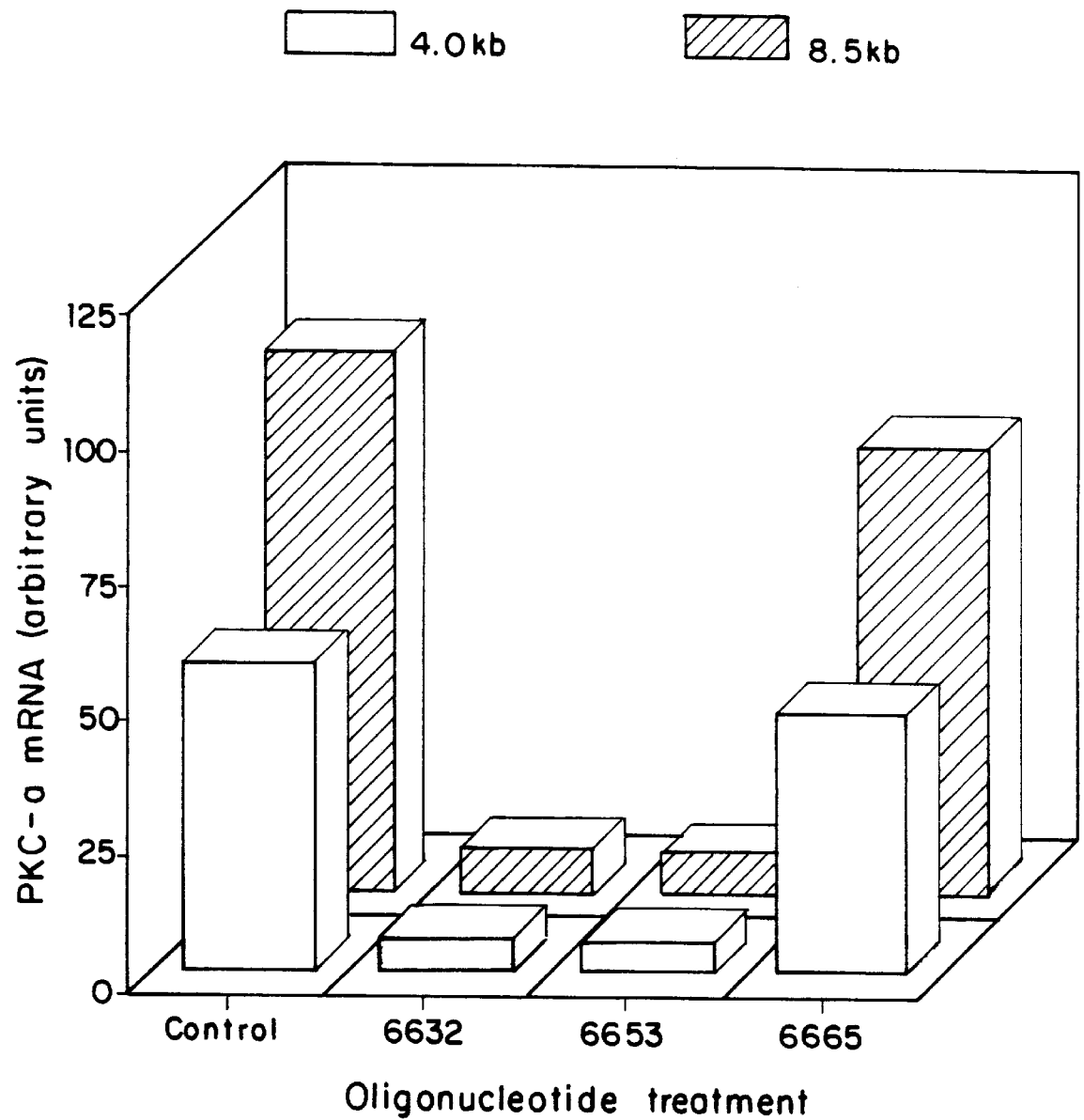
FIG. 9A shows oligonucleotides 6632, 6653 and 6665.
Figure 9B:
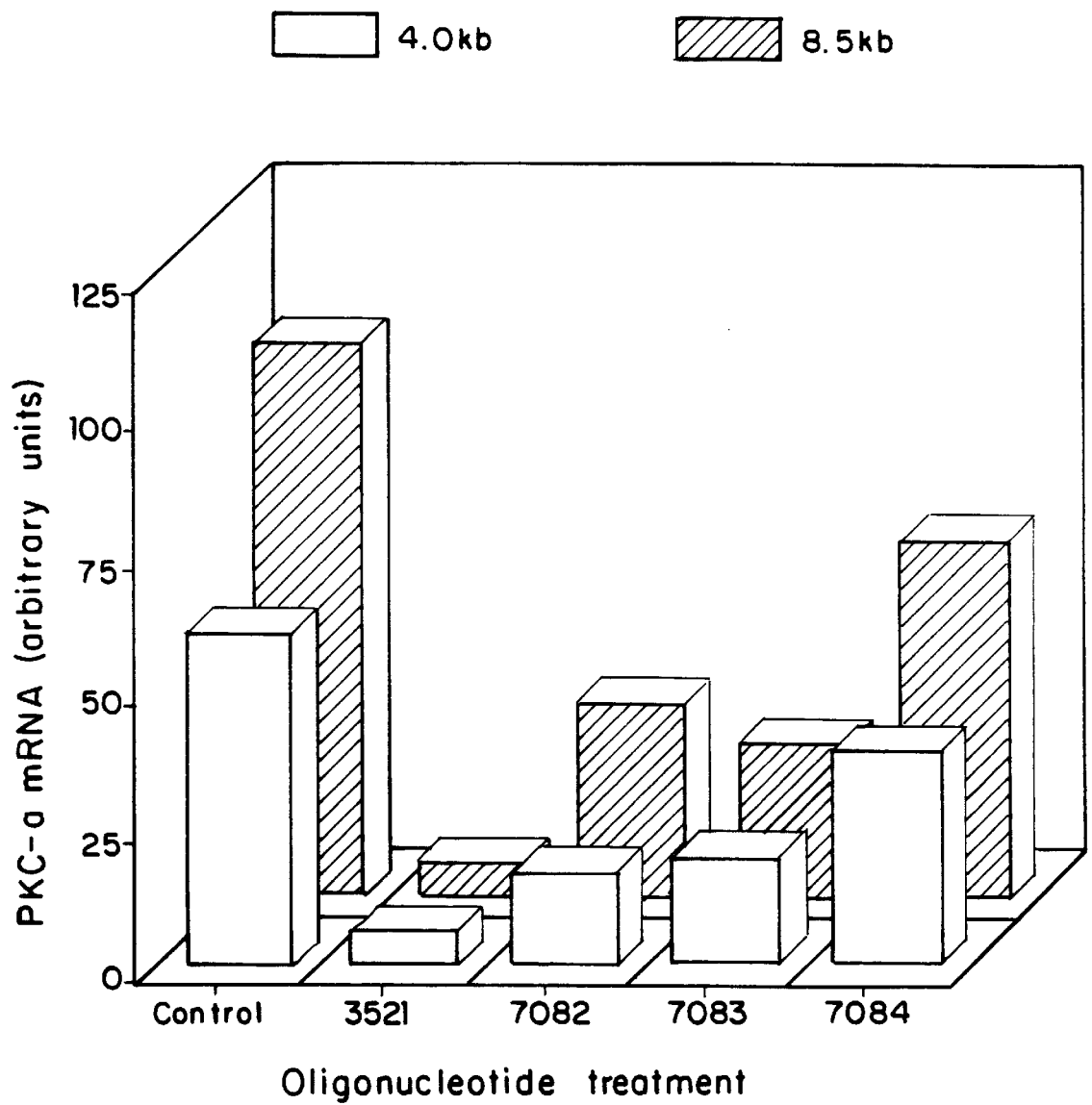
FIG. 9B shows oligonucleotides 3521 (for comparison), 7082, 7083 and 7084. Hatched bars represent the 8.5 kb transcript, plain bars represent the 4.0 kb transcript.

As shown in FIG. 9, oligonucleotides 6632, 6653, 7082 and 7083 are most active in reducing PKC-α mRNA levels.

Example 9
Culture of human A549 lung tumor cells

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Cells were trypsinized and washed and resuspended in the same medium for introduction into mice.

Example 10
Effect of ISIS 3521 on the growth of human A549 lung tumor cells in nude mice 200 μl of A549 cells (5×10$^6$ cells) were implanted subcutaneously in the inner thigh of nude mice. ISIS 3521, a phosphorothioate oligonucleotide with Sequence ID NO 2 was administered twice weekly for four weeks, beginning one week following tumor cell inoculation. Oligonucleotides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

As shown in FIG. 10, tumor growth was almost completely inhibited in two of the three mice, and reduced compared to control in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

Figure 11A:
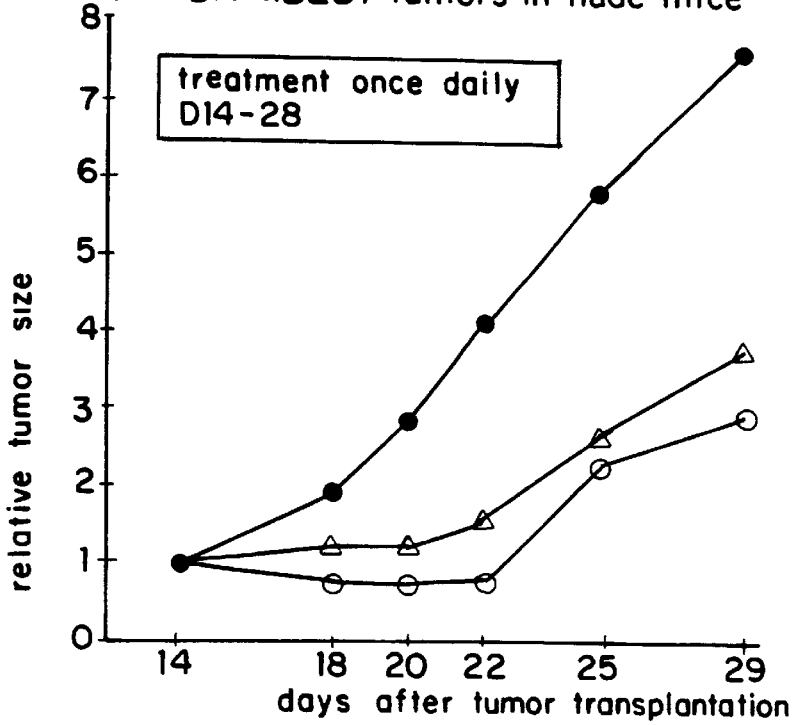
FIG. 11A shows results obtained with ISIS 3521.
Figure 11B:
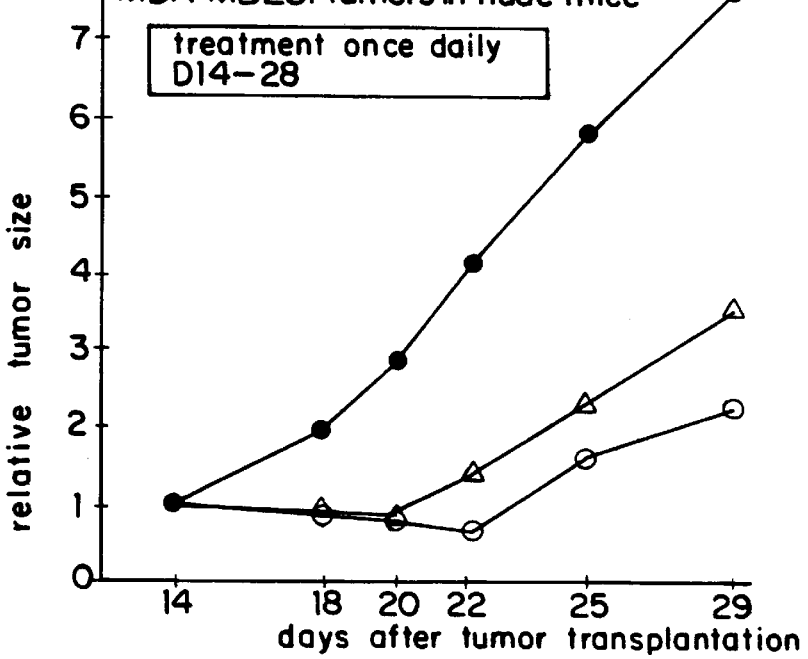
FIG. 11B shows results obtained with ISIS3527. Each line represents tumor volume in one animal. ●=control; ○=oligonucleotide at 60 mg/kg ; Δ=oligonucleotide at 6 mg/kg.

Example 11
Effect of antisense oligonucleotides on growth of human MDA-MB231 tumors in nude mice MDA-MB231 human breast carcinoma cells were obtained from the American Type Culture Collection (Bethesda, Md.). Serially transplanted MDA-MB231 tumors were established subcutaneously in nude mice. Beginning two weeks later, oligonucleotides 3521 and 3527, a phosphorothioate oligonucleotide having Sequence ID NO. 5, in saline, were administered intravenously daily for 14 days at dosages of 60 mg/kg and 6 mg/kg. Control oligonucleotide ISIS 1082 was also administered at these doses, and a saline control was also given. Tumor growth rates were monitored for the two-week period of oligonucleotide administration. As shown in FIG. 11, both PKC-α oligonucleotides (3521 and 3527) significantly inhibit tumor growth at dosages of 60 mg/kg and 6 mg/kg. The control oligonucleotide (ISIS 1082) also showed some reduction in tumor growth, but this effect was less than with antisense oligonucleotides even at high doses, and considerably less at the lower dose. A lower-dose study was conducted using the same oligonucleotides at 6 mg/kg and 0.6 mg/kg. At 0.6 mg/kg ISIS 3521 significantly reduced tumor growth. At this concentration, ISIS 3527 also reduced tumor growth, but this result was not statistically significant.

Example 12
Effect of oligonucleotides on the growth of murine Lewis lung carcinoma in mice Serially transplanted murine Lewis lung carcinomas were established in mice. Oligonucleotides 3521 and 3527 were administered intravenously every day for 14 days at doses of 6 mg/kg and 0.6 mg/kg. Tumor growth rates were monitored for the two-week period of oligonucleotide administration. As expected, these oligonucleotides, which are targeted to human PKC sequences, had insignificant effects on the mouse-derived tumors.

Example 13
Effects of antisense oligonucleotide ISIS 4189 on endogenous PKC-α expression in hairless mice In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an IC50 of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 14
Screening of antisense oligonucleotides targeted to human PKC-η

Figure 12:
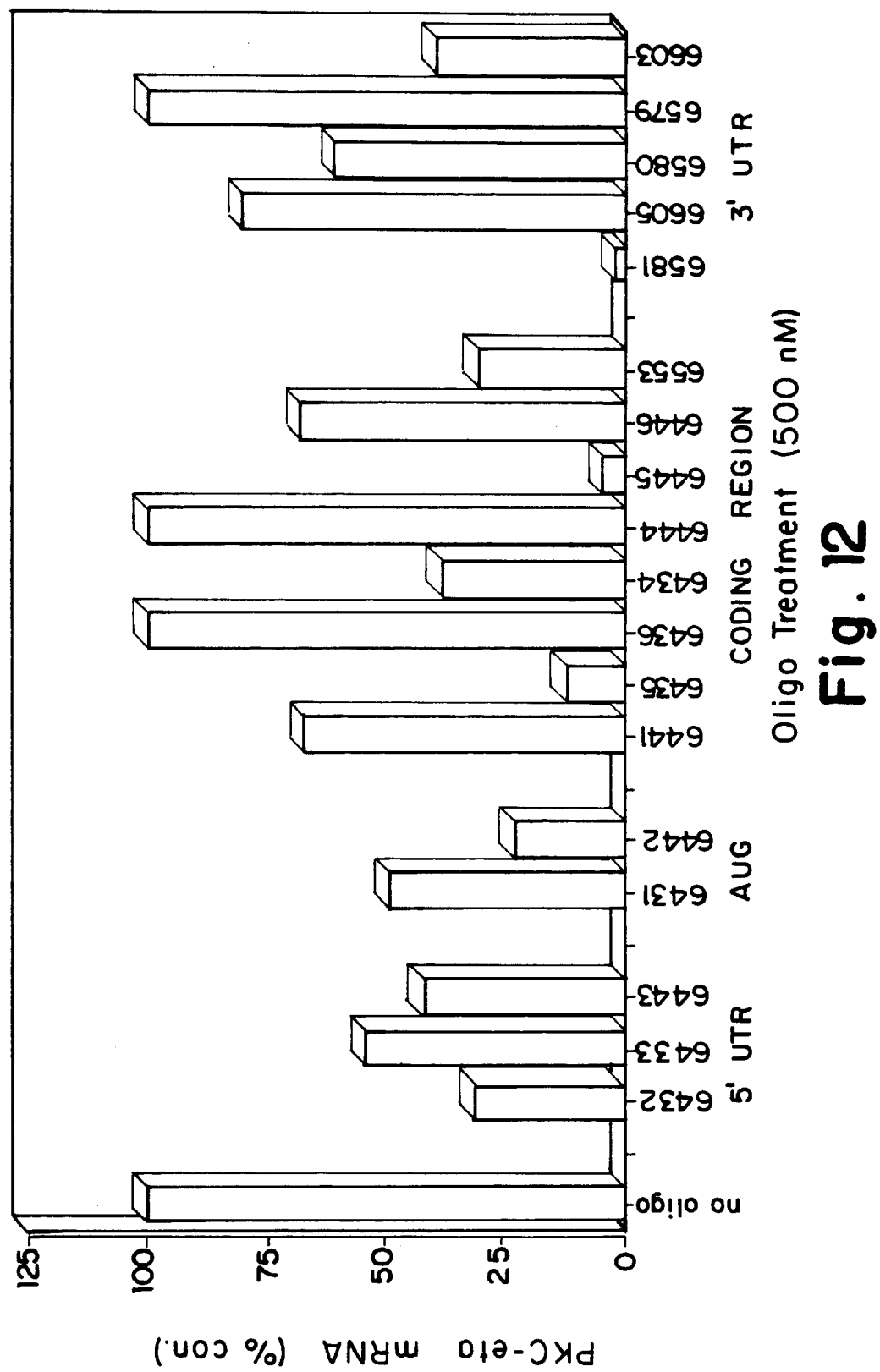
FIG. 12 is a bar graph showing effect of 20-mer phosphorothioate oligonucleotides on PKC-η expression in A549 cells.

A series of 20-mer phosphorothioate oligonucleotides complementary to human PKC-η were synthesized. These oligonucleotides were screened at a concentration of 500 nM for ability to decrease PKC-η mRNA levels in human A549 cells, using a Northern blot assay. The oligonucleotide sequences are shown in Table 10 and the results are shown in FIG. 12.

TABLE 10

OLIGONUCLEOTIDES TARGETED TO HUMAN PKC-η mRNA

| SEQ ID | Sequence | Target | ISIS # |
|---|---|---|---|
| 6431 | CGA CAT GCC GGC GCC GCT GC | AUG | 40 |
| 6442 | CAG ACG ACA TGC CGG CGC CG | AUG | 41 |
| 6443 | GCC TGC TTC GCA GCG GGA GA | 5' UTR | 42 |
| 6432 | ACA GGT GCA GGA GTC GAG GC | 5' UTR | 43 |
| 6433 | GTC CCG TCT CAG GCC AGC CC5' | UTR | 44 |

TABLE 10-continued

OLIGONUCLEOTIDES TARGETED TO HUMAN PKC-η mRNA

| SEQ ID | Sequence | Target | ISIS # |
|---|---|---|---|
| 6435 | CCT CAC CGA TGC GGA CCC TC | Coding | 45 |
| 6441 | ATT GAA CTT CAT GGT GCC AG | Coding | 46 |
| 6581 | TCT CAC TCC CCA TAA GGC TA | 3' UTR | 47 |
| 6580 | TTC CTT TGG GTT CTC GTG CC | 3' UTR | 48 |
| 6436 | AAC TCG AGG TGG CCG CCG TC | Coding | 54 |
| 6434 | CGC CTT CGC ATA GCC CTT TG | Coding | 55 |
| 6444 | GGA AGG GGT GAT TGC GGG CC | Coding | 56 |
| 6445 | AAC ACG CCC ATT GCC CAC CA | Coding | 57 |
| 6446 | GTC TCA AGA TGG CGT GCT CG | Coding | 58 |
| 6553 | GCG ATG GTT CAG CTG GGC CC | Coding | 59 |
| 6605 | GCC CTC TCT CTC ACT CCC CA | 3' UTR | 60 |
| 6579 | CTG GGA AGG TCC GAT AGA GG | 3' UTR | 61 |
| 6603 | AAG GCT GAT GCT GGG AAG GT | 3' UTR | 62 |

Oligonucleotides 6432, 6443, 6431, 6442, 6435, 6434, 6445, 6553, 6581 and 6603 reduced PKC-η mRNA levels by greater than 50%. The most potent oligonucleotides were ISIS 6581 (targeting 3' untranslated region) and ISIS 6445 (targeting coding region) which gave nearly complete loss of PKC mRNA in this assay.

Example 15
Screening of antisense oligonucleotides targeted to PKC-δ

A series of 20-mer phosphorothioate oligonucleotides complementary to human PKC-δ were synthesized. These oligonucleotides were screened by Northern blot assay at a concentration of 500 nM for their ability to decrease PKC-δ mRNA levels in human A549 cells. The oligonucleotide sequences and the results, expressed as percent inhibition of PKC-δ mRNA expression, are shown in Table 11.

TABLE 11

Antisense oligonucleotides targeted to PKC-δ

| Isis # | Site | Sequence | % Inhib | SEQ ID: |
|---|---|---|---|---|
| 10299 | AUG | GCA GGA ACG GCG CCA TGG TG | 0% | 63 |
| 10300 | Coding | CTG GTT CGC CTC GTC CTC GG | 25 | 64 |
| 10301 | Coding | ATC TGG ATG ACG CGC CCC TC | 26 | 65 |
| 10302 | Coding | TTC TTG CAG CGC TCG GCC AG | 8 | 66 |
| 10303 | Coding | TGC AAT CCA CGT CCT CCA GG | 50 | 67 |
| 10304 | Coding | GGC TCC GCG GCG GTT CAT CG | 12 | 68 |
| 10305 | Coding | AAG CGG TGC GGC ATG TCG AT | 43 | 69 |
| 10306 | Coding | GCA GGC TGC CGC AGT GGT CA | 12 | 70 |
| 10307 | Coding | CCT CCC CAG CAA CTC CGG TC | 36 | 71 |
| 10308 | Coding | AGC GGC CTT TGT CCT GGA TG | 11 | 72 |
| 10309 | Coding | GGC CAT CCC GGT CCA ACA GC | 43 | 73 |
| 10310 | Coding | GGT GCT GGC CCG GCT CTC CC | 66 | 74 |
| 10311 | Coding | GGA CCC CGA AAG ACC ACC AG | 77 | 75 |
| 10312 | Coding | GTG GCT CCA ACC TCC GCT TT | 18 | 76 |
| 10313 | Coding | AGG AGG TGC TCG AAT TTG GG | 0% | 77 |

Oligonucleotides ISIS 10303, ISIS 10310 and ISIS 10311 gave at least 50% inhibition of PKC-δ mRNA expression in this assay and are preferred.

Example 16
Screening of antisense oligonucleotides targeted to PKC-ε

A series of 20-mer phosphorothioate oligonucleotides complementary to human PKC-ε were synthesized. These oligonucleotides were screened by Northern blot assay at a concentration of 500 nM for their ability to decrease PKC-ε mRNA levels in human A549 cells. The oligonucleotide sequences and the results, expressed as percent inhibition of PKC-ε mRNA expression, are shown in Table 12.

TABLE 12

Antisense oligonucleotides targeted to PKC-ε

| Isis # | Site | Sequence | % Inhib | SEQ ID: |
|---|---|---|---|---|
| 7933 | AUG | ACT ACC ATG GTC GGG GCG GG | 0% | 78 |
| 7934 | Coding | GTC CCA CCG CAT GGC GCA GC | 0 | 79 |
| 7935 | Coding | GTT TGG CCG ATG CGC GAG TC | 0 | 80 |
| 7936 | Coding | TGC AGT TGG CCA CGA AGT CG | 0 | 81 |
| 8032 | Coding | GTG GGG CAT GTT GAC GCT GA | 0 | 82 |
| 8031 | Coding | CCA GAG CAG GGA CCC ACA GT | 0 | 83 |
| 7939 | Coding | TCT CCT CGG TTG TCA AAT GA | 0 | 84 |
| 7940 | Coding | CGG TGC TCC TCT CCT CGG TT | 0 | 85 |
| 7941 | Coding | AGC CAA AAT CCT CTT CTC TG | 0 | 86 |
| 7942 | Coding | CAT GAG GGC CGA TGT GAC CT | 67 | 87 |
| 7943 | Coding | ATC CCT TCC TTG CAC ATC CC | 3 | 88 |
| 7944 | Coding | CCC CAG GGC CCA CCA GTC CA | 38 | 89 |
| 7945 | Coding | AGC ACC CCC AGG GCC CAC CA | 42 | 90 |
| 7946 | Coding | CGT ACA TCA GCA CCC CCA GG | 42 | 91 |
| 7947 | Coding | CCA GCC ATC ATC TCG TAC AT | 9 | 92 |
| 7948 | Coding | TGC CAC ACA GCC CAG GCG CA | 55 | 93 |
| 7949 | Stop | TCA GGG CAT CAG GTC TTC AC | 0 | 94 |
| 7950 | Stop | CTC TCA GGG CAT CAG GTC TT | 0 | 95 |

Oligonucleotides ISIS 7942 and ISIS 7948 gave at least 50% inhibition of PKC-ε mRNA expression in this assay and are preferred.

Additional oligonucleotides targeted to PKC-ε were synthesized. These are shown in Table 13.

TABLE 13

Antisense oligonucleotides targeted to PKC-ε

| Isis # | Site | Sequence | SEQ ID: |
|---|---|---|---|
| A | Coding | AAG GAA AGT CTG CGG CCG GG | 96 |
| B | Coding | TGG CGG CTC CCG TTC TGC AG | 97 |
| C | Coding | GCT TCC TCG GCC GCA TGC GT | 98 |
| D | Coding | TTG ACG CTG AAC CGC TGG GA | 99 |
| E | Coding | GCC CGG TGC TCC TCT CCT CG | 100 |
| F | Coding | GGG CCG ATG TGA CCT CTG CA | 101 |
| G | Coding | TGG AGG AAC ATG AGG GCC GA | 102 |
| H | Coding | CCC CCA GGG CCC ACC AGT CC | 103 |
| I | Coding | TGC GAT GCC ACA CAG CCC AG | 104 |
| J | Stop | TGG GCT CTC AGG GCA TCA GG | 105 |

Example 17
Screening of antisense oligonucleotides targeted to PKC-ζ

A series of 20-mer phosphorothioate oligonucleotides complementary to human PKC-ζ were synthesized. These oligonucleotides were screened by Northern blot assay at a concentration of 500 nM for their ability to decrease PKC-ζ mRNA levels in human A549 cells. The oligonucleotide sequences and the results, expressed as percent inhibition of PKC-ζ mRNA expression, are shown in Table 14.

TABLE 14

Antisense oligonucleotides targeted to PKC-ζ

| Isis # | Site | Sequence | % Inhib | SEQ ID: |
|---|---|---|---|---|
| 9007 | AUG | CGC CGC TCC CTT CCA TCT TG | 67% | 106 |
| 9008 | Coding | CCC CGT AAT GCG CCT TGA GG | 64 | 107 |
| 9009 | Coding | CTG TCC ACC CAC TTG AGG GT | 14 | 108 |
| 9012 | Coding | TTG GAA GAG GTG GCC GTT GG | 78 | 109 |
| 9013 | Coding | CCT GTT AAA GCG CTT GGC TT | 67 | 110 |
| 9014 | Coding | TGC AGG TCA GCG GGA CGA GG | 40 | 111 |
| 9016 | Coding | AGC CCC TGA GAG ATT TTG AT | 0 | 112 |
| 9017 | Coding | TTC TTC AAC CGC ACC AGG AG | 67 | 113 |

TABLE 14-continued

Antisense oligonucleotides targeted to PKC-ζ

| Isis # | Site | Sequence | % Inhib | SEQ ID: |
|---|---|---|---|---|
| 9019 | Coding | TCC TTG CAC ATG CCG TAG TC | 24 | 114 |
| 9021 | Coding | GGA GCG CCC GGC CAT CAT CT | 78 | 115 |
| 9022 | Coding | GGG CTC GCT GGT GAA CTG TG | 85 | 116 |
| 9023 | 3' UTR | GAC GCA CGC GGC CTC ACA CC | 88 | 117 |
| 9025 | 3' UTR | TCG GAG CCG TGC CCA GCC TG | 88 | 118 |
| 9026 | 3' UTR | CGG GCC AGG TGT GAG GGA CT | 40 | 119 |
| 9027 | 3' UTR | CCG CGA CGC AGG CAC AGC AG | 40 | 120 |
| 9029 | 3' UTR | GGT CAG TGC ATC GAG TTC TG | 77 | 121 |

Oligonucleotides ISIS 9007, 9008, 9012, 9013, 9017, 9021, 9022, 9023, 9025 and 9029 gave greater than 50% inhibition of PKC-ζ mRNA expression in this assay and are preferred. Of these, ISIS 9022, ISIS 9023 and ISIS 9025 gave at least 85% inhibition and are more preferred.

Example 18
Effect of ISIS 3521 on the growth of human T24 bladder tumors in nude mice Subcutaneous human T24 bladder carcinoma xenografts in nude mice were established by injection of $5 \times 10^6$ T24 cells under the skin. Mice were treated with ISIS 3521 or ISIS 4559, a phosphorothioate scrambled version of the ISIS 3521 sequence, or ISIS 1082, an unrelated control phosphorothioate oligonucleotide targeted to Herpes simplex virus (oligonucleotide doses 0.006 mg/kg, 0.06 mg/kg, 0.6 mg/kg or 6.0 mg/kg) or saline administered intraperitoneally three times weekly. By day 21, ISIS 1082 or ISIS 4559 had no effect on tumor growth at any dose. By day 21, ISIS 3521 showed a dose-dependent inhibition of tumor growth at all dose levels, with a maximal inhibition of 90% at the 6 mg/kg dose.

Example 19
Effect of ISIS 3521 on the growth of human Colo-205 colon tumors in nude mice Subcutaneous human Colo-205 colon carcinoma xenografts in nude mice were established by injection of $5 \times 10^6$ Colo-205 cells under the skin. Mice were treated with ISIS 3521 and an unrelated control phosphorothioate oligonucleotide (ISIS 1082) administered intravenously once per day at a dosage of 6.0 mg/kg. In this study, ISIS 3521 inhibited tumor growth after 25 days by 84% compared to saline controls. The control oligonucleotide, ISIS 1082, inhibited tumor growth by 20%.

Figure 13:
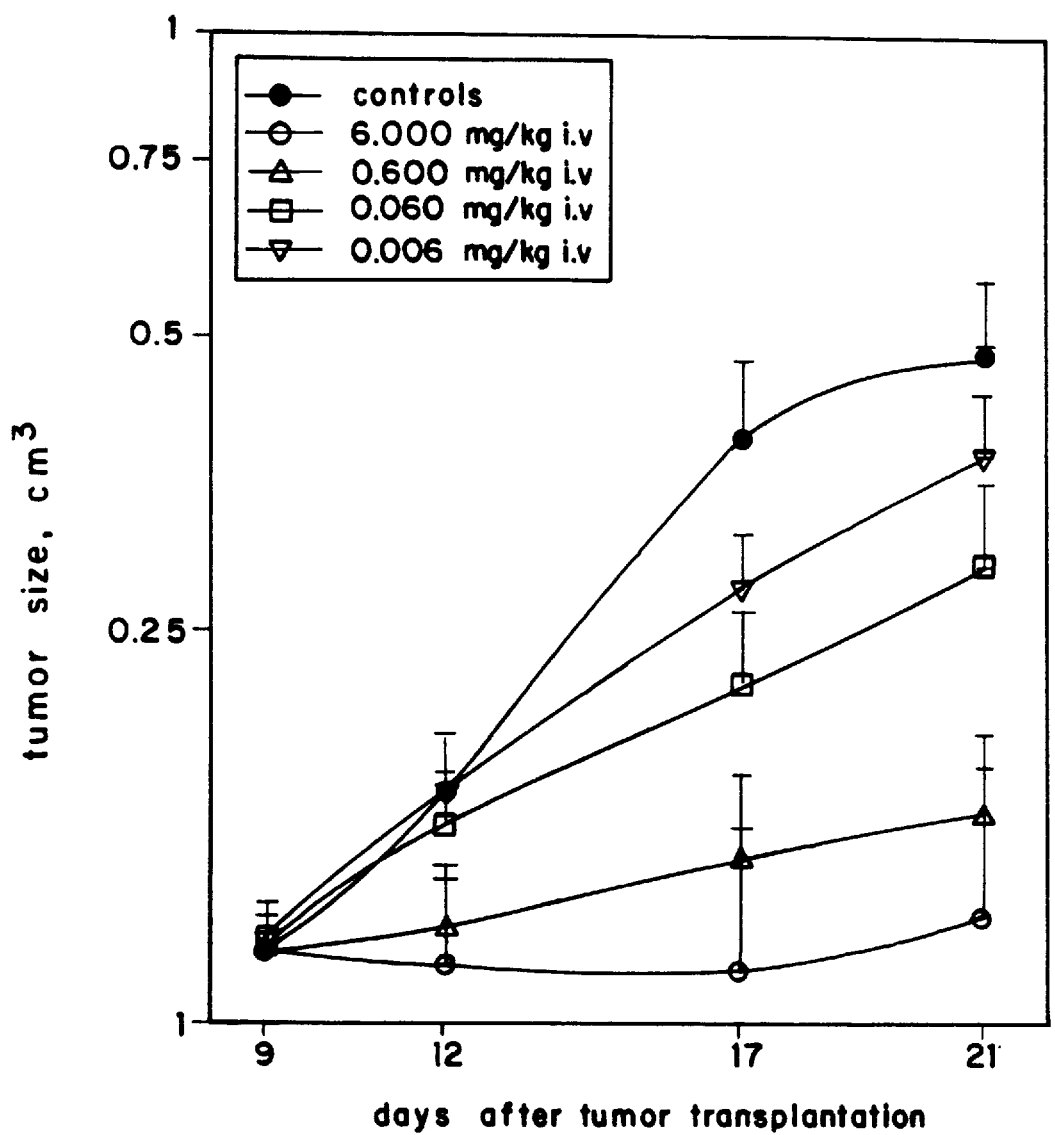
FIG. 13 is a line graph showing the effect of ISIS 8459 (2' fluoro gapped version of ISIS 3521) on the growth of A549 xenografts in nude mice. All doses (0.006, 0.06, 0.6. 6.0 mg/kg) of ISIS 8459 inhibit tumor growth.

Example 20
Effect of ISIS 8469, a 2'-fluoro gapped version of ISIS 3521, on the growth of A549 human lung tumors in nude mice Subcutaneous human A549 lung adenocarcinoma xenografts were established by injection of $5 \times 10^6$ A549 cells under the skin of Balb/c nude mice. Mice were treated with ISIS 8469, a chimeric version of ISIS 3521 having an 8-nucleotide deoxy gap flanked by six 2'-fluoro nucleotides on each side, as in Example 10. Oligonucleotide doses were from 0.006 mg/kg to 6.0 mg/kg. ISIS 8469 decreased tumor size at all doses in a dose-dependent manner, as shown in FIG. 13. This compound is therefore preferred.

Example 21
U-87 human glioblastoma cell culture and subcutaneous xenografts into nude mice The U-87 human glioblastoma cell line was obtained from the ATCC (Rockville Md.) and maintained in Iscove's DMEM medium supplemented with heat-inactivated 10% fetal calf serum. Nude mice were injected subcutaneously with 2×10$^7$ cells. Mice were injected intraperitoneally with ISIS 3521 at dosages of either 2 mg/kg or 20 mg/kg for 21 consecutive days beginning 7 days after xenografts were implanted. Tumor volumes were measured on days 14, 21, 24, 31 and 35. On day 35 (7 days after end of treatment), ISIS 3521 at 2 mg/kg had reduced tumor volume by 84% compared to saline or sense oligonucleotide control. The 20 mg/kg dose reduced tumor size by 91% on day 35.

Example 22

Effect of ISIS 3521 on PKC-α protein levels in U-87 glioblastoma xenografts in nude mice PKCα protein levels in subcutaneous U-87 tumor xenografts were measured by western blot analysis on day 24 (day 17 of treatment with ISIS 3521) and day 35 (7 days after end of treatment with ISIS 3521). An affinity-purified PKCα-specific polyclonal antibody (Life Technologies, Inc.) was used as the primary antibody. By day 24, ISIS 3521 was found to virtually totally abolish PKCα in the tumors. By seven days after cessation of oligonucleotide treatment (day 35), PKCα had returned to control levels.

Example 23

"Crossover experiment" to evaluate effect of switching treatment on tumor size

Figure 14:
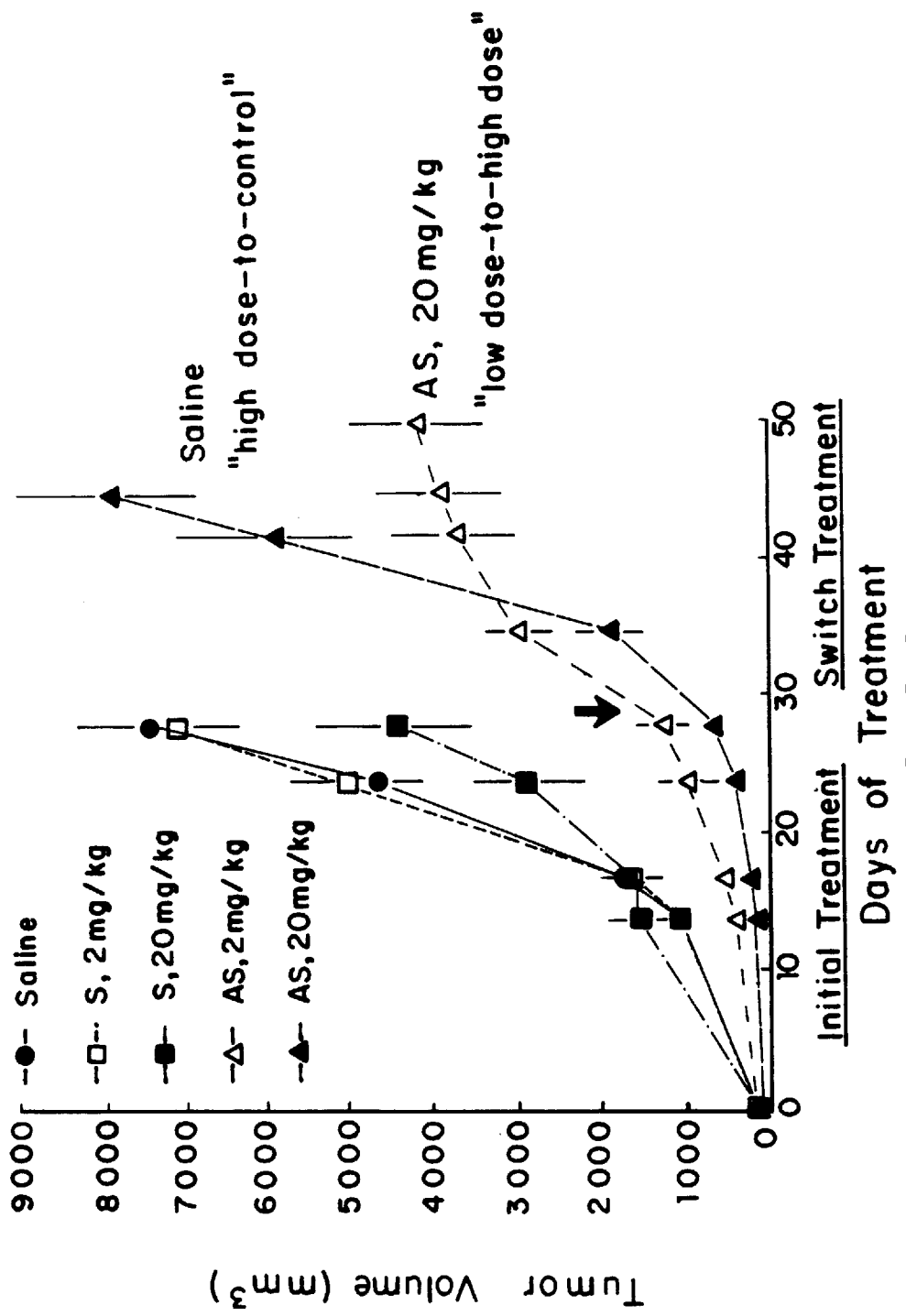
FIG. 14 is a line graph showing a "crossover" experiment to evaluate the effect of ISIS 3521 on U-87 glioblastoma cells in nude mice. The experiment was carried out with oligonucleotide doses of 2 mg/kg and 20 mg/kg and then treatment was switched (arrow). The group which had originally received ISIS 3521 at 20 mg/kg ("high dose-to-control" group, closed triangles) then received saline and the group which had originally received ISIS 3521 at 2 mg/kg ("low dose-to-high dose", open triangles) then received ISIS 3521 at 20 mg/kg. S=sense oligonucleotide (control); AS=antisense oligonucleotide (ISIS 3521) targeted to PKCα.

The two groups of mice with subcutaneous U-87 xenografts previously treated with ISIS 3521 (2 mg/kg or 20 mg/kg) were switched to different treatments on day 35 (7 days after the initial 21 day treatment had ended). The group which had previously received 20 mg/kg ISIS 3521 now received saline ("high dose-to-control"). The group which had received 2 mg/kg ISIS 3521 now received 20 mg/kg ISIS 3521 ("low dose-to-high dose"). This crossover treatment was continued for 21 days as for the original treatment. As shown in FIG. 14, the growth of the tumors in the "low dose-to-high dose" group (open triangles) leveled off after treatment was switched (arrow). The growth of the tumors in the "high dose-to-control" group (closed triangles) rapidly accelerated after switching to saline treatment (arrow). S=sense oligonucleotide (control); AS=antisense oligonucleotide (ISIS 3521) targeted to PKCα.

Example 24

Effect of ISIS 3521 on intracerebral U-87 glioblastoma xenografts into nude mice U-87 cells how were implanted in the brains of nude mice. Mice were treated via continuous intraperitoneal administration of antisense oligonucleotide ISIS 3521 (20 mg/kg), control sense oligonucleotide (20 mg/kg) or saline beginning on day 7 after xenograft implantation. All mice survived until day 25, at which point the saline-treated mice began to die. All saline-treated mice and sense oligonucleotide-treated mice were dead by day 41. In contrast, all ISIS 3521-treated mice were alive until approximately day 37, and half of the mice were still alive at day 61. At the termination of the experiment at day 80, 40% of the ISIS 3521-treated mice were still alive.

Example 25

Preparation of 2'-Deoxy-2'-fluoro Modified Oligonucleotides

A. N$^6$-Benzoyl-[2'-deoxy-2'-fluoro-5'-O-(4,4'-di-methoxy trityl)] adenosine-3'-O-(N,N-diisopropyl -β-cyanoethyl phosphoramidite N$^6$-Benzoyl-9-(2'-fluoro-b-D-ribofuranosyl) adenine was prepared from 9-b-D-arabinofuranosyladenine in a five-step synthesis using a modification of a procedure reported by M. Ikehara et al., *Nucleosides and Nucleotides* 2:373–385 (1983). Thus, the N$^6$-benzoyl derivative was obtained in good yield utilizing the method of transient protection with chlorotrimethylsilane. R. A. Jones, *J. Am. Chem. Soc.* 104:1316 (1982). Selective protection of 3' and 5'-hydroxyl groups of N-$^6$-Benzoyl-9-β-D-arabinofuranosyladenine with tetrahydro-pyranyl (THP was accomplished by modification of a literature procedure G. Butke, et al., in *Nucleic Acid Chemistry*, Part 3:149–152, Townsend, L. B. and Tipson, R. S. eds., (J. Wiley and Sons, New York 1986) to yield N$^6$-Benzoyl-9-[3',5'-di-O-tetrahydropyran-2-yl)-β-D-arabino furanosyl] adenine in good yield. Treatment of N$^6$-Benzoyl-9-[3',5'-di-O-tetrahydropyran-2-yl)-β-D-arabinofuranosyl] adenine with trifluoro-methanesulfonic anhydride in dichloromethane gave the 2'-tri-flate derivative N$^6$-Benzoyl-9-[2'-O-trifluoromethylsulfonyl-3',5'-di-O-tetrahydropyran-2-yl)-β-D-arabino furanosyl]adenine which was not isolated due to its liability. Displacement of the 2'-triflate group was effected by reaction with tetra-butylammonium fluoride in tetrahdyrofuran to obtain a moderate yield of the 2'-fluoro derivative N$^6$-Benzoyl-9-[2'-fluoro-3',5'-di-O-tetrahydropyran-2-yl)-β-D-arabino furanosyl]-adenine. Deprotection of the THP groups of N$^6$-Benzoyl-9-[2'-fluoro-3',5'-di-O-tetrahydropyran-2-yl)-β-D-arabinofuranosyl]adenine was accomplished by treatment with Dowex-50W in methanol to yield N$^6$-benzoyl-9-(2'-deoxy -2'-fluoro-β-D- ribofuranosyl)adenine in moderate yield. The $^1$H-NMR spectrum of 6 was in agreement with the literature values. M. Ikehara and H. Miki, *Chem. Pharm. Bull.* 26:2449–2453 (1978). Standard methodologies were employed to obtain the 5'-dimethoxytrityl-3'-phosphoramidite intermediates N$^6$-Benzoyl-9-[2'-fluoro-5'-O-(4,4'-dimethoxytrityl)-β-D-ribofuranosyl]adenine and N$^6$-Benzoyl-[2'-deoxy-2'-fluoro -5'-O-(4,4'-dimethoxy-trityl)] adenosine-3'-O-(N,N-diisopropyl-β-cyanoethyl-phosphoramidite. K. K. Ogilvie, *Can J. Chem.* 67:831–839 (1989).

B. N$^6$-Benzoyl-9-β-D-arabinofuranosyladenine

9-β-D-arabinofuranosyladenine (1.07 g, 4.00 m.mol) was dissolved in anhydrous pyridine (20 mL) and anhydrous dimethylformamide (20 ml) under an argon atmosphere. The solution was cooled to ice temperature and chlorotrimethyl-silane (3.88 ml, 30.6 m.mol) was added slowly to the reaction mixture via syringe. After stirring the reaction mixture at ice temperature for 30 minutes, benzoyl chloride (2.32 ml, 20 m.mol) was added slowly. The reaction mixture was allowed to warm to 20° C. and stirred for 2 hours. After cooling the reaction mixture to ice temperature, cold water (8 ml) was added and the mixture was stirred for 15 minutes. Concentrated ammonium hydroxide (8 ml) was slowly added to the reaction mixture to give a final concentration of 2M of ammonia. After stirring the cold reaction mixture for 30 minutes, the solvent was evaporated in vacuo (60 torr) at 20° C. followed by evaporation in vacuo (1 torr) at 40° C. to give an oil This oil was triturated with diethyl ether (50 ml) to give a solid which was filtered and washed with diethyl ether three times. This crude solid was triturated in methanol (100 ml) at reflux temperature three times and the solvent was evaporated to yield $N^6$-Benzoyl-9-β-D-arabinofuranosyladenine as a solid (1.50 g, 100%).

C. $N^6$-Benzoyl-9-[3',5'-di-O-tetrahydropyran-2-yl)-β-D-arabino furanosyl] adenine $N^6$-Benzoyl-9-β-D-arabinofuranosyladenine (2.62 g, 7.06 m.mol) was dissolved in anhydrous dimethylformamide (150 ml) under an argon atmosphere and p-toluenesulfonic acid monohydrate (1.32 g, 6.92 m.mol) was added. This solution was cooled to ice temperature and dihydropyran (1.26 ml, 13.8 m.mol) was added via syringe. The reaction mixture was allowed to warm to 20° C. Over a period of 5 hours a total of 10 equivalents of dihydropyran were added in 2 equivalent amounts in the fashion described. The reaction mixture was cooled to ice temperature and saturated aqueous sodium bicarbonate was added slowly to a pH of 8, then water was added to a volume of 750 ml. The aqueous mixture was extracted with methylene chloride four times (4×200 ml), and the organic phases were combined and dried over magnesium sulfate. The solids were filtered and the solvent was evaporated in vacuo (60 torr) at 30° C. to give a small volume of liquid which was evaporated in vacuo (1 torr) at 40° C. to give an oil. This oil was coevaporated with p-xylene in vacuo at 40° to give an oil which was dissolved in methylene chloride (100 ml). Hexane (200 ml) was added to the solution and the lower-boiling solvent was evaporated in vacuo at 300° C. to leave a white solid suspended in hexane. This solid was filtered and washed with hexane three times (3×10 ml) then purified by column chromatography using silica and methylene chloride-methanol (93:7, v/v) as eluent. The first fraction yielded the title compound 3 as a white foam (3.19 g, 83%) and a second fraction gave a white foam (0.81 g) which was characterized as the 5'-mono-tetrahydropyranyl derivative of $N^6$-Benzoyl-9-β-D-arabinofuranosyladenine.

D. $N^6$-Benzoyl-9-[2'-O-trifluoromethylsulfonyl-3',5'-di-O-tetrahydropyran-2-yl)-β-D-arabinofuranosyl] adenine $N^6$-Benzoyl-9-[3',5'-di-O-tetrahydropyran-2-yl) β-D-arabinofuranosyl] adenine (2.65 g, 4.91 m.mol) was dissolved in anhydrous pyridine (20 ml) and the solvent was evaporated in vacuo (1 mm Hg) at 40° C. The resulting oil was dissolved in anhydrous methylene chloride (130 ml) under an argon atmosphere and anhydrous pyridine (3.34 ml, 41.3 m.mol) and N,N-dimethylaminopyridine (1.95 g, 16.0 mmol) were added. The reaction mixture was cooled to ice temperature and trifluoromethanesulfonic anhydride (1.36 ml, 8.05 mmol) was added slowly via syringe. After stirring the reaction mixture at ice temperature for 1 h, it was poured into cold saturated aqueous sodium bicarbonate (140 ml). The mixture was shaken and the organic phase was separated and kept at ice temperature. The aqueous phase was extracted with methylene chloride two more times (2×140 ml). The organic extracts which were diligently kept cold were combined and dried over magnesium sulfate. The solvent was evaporated in vacuo (60 torr) at 20° C. then evaporated in vacuo (1 torr) at 20° C. to give $N^6$-Benzoyl-9-[2'-O-trifluoromethylsulfonyl-3',5'-di-O-tetrahydropyran-2-yl)-β-D-arabinofuranosyl] adenine as a crude oil which was not purified further.

E. $N^6$-Benzoyl-9-[2'-fluoro-3',5'-di-O-tetrahydro-pyran-2-yl)-β-D-arabinofuranosyl]adenine $N^6$-Benzoyl-9-[2'-O-trifluoromethylsulfonyl-3',5'-di-O-tetrahydropyran-2-yl)-β-D-arabinofuranosyl] adenine (<4.9 mmol) as a crude oil was dissolved in anhydrous tetrahydrofuran (120 ml) and this solution was cooled to ice temperature under an argon atmosphere Tetrabutylammonium fluoride as the hydrate (12.8 g, 49.1 mmol) was dissolved in anhydrous tetrahydrofuran (50 ml) and half of this volume was slowly added via syringe to the cold reaction mixture. After stirring at ice temperature for 1 hour, the remainder of the reagent was added slowly. The reaction mixture was stirred at ice temperature for an additional 1 hour, then the solvent was evaporated in vacuo (60 torr) at 20° C. to give an oil. This oil was dissolved in methylene chloride (250 ml) and washed with brine three times. The organic phase was separated and dried over magnesium sulfate. The solids were filtered and the solvent was evaporated to give an oil. The crude product was purified by column chromatography using silica in a sintered-glass funnel (600 ml) and ethyl acetate was used as eluent. $N^6$-Benzoyl-9-[2'-fluoro-3',5'-di-O-tetrahydropyran-2-yl)-β-D-arabinofuranosyl]adenine was obtained as an oil (2.03 g, 76%).

F. $N^6$-Benzoyl-9-(2'-fluoro-β-D-ribofuranosyl)adenine $N^6$-Benzoyl-9-[2'-fluoro-3',5'-di-O-tetrahydro-pyran-2-yl)-β-D-arabinofuranosyl]adenine (1.31 g, 2.42 mmol) was dissolved in methanol (60 ml), and Dowex 50W×2-100 (4 cm3, 2.4 m.eq) was added to the reaction mixture. The reaction mixture was stirred at 20° C. for 1 hour then cooled to ice temperature. Triethylamine (5 ml) was then slowly added to the cold reaction mixture to a pH of 12. The resin was filtered and washed with 30% triethylamine in methanol until the wash no longer contained UV absorbing material. Toluene (50 ml) was added to the washes and the solvent was evaporated at 24° C. in vacuo (60 torr then 1 torr) to give a residue. This residue was partially dissolved in methylene chloride (30 ml) and the solvent was transferred to a separatory funnel. The remainder of the residue was dissolved in hot (60° C.) water and after cooling the solvent it was also added to the separatory funnel. The biphasic system was extracted, and the organic phase was separated and extracted three times with water (3×100 ml). The combined aqueous extracts were evaporated in vacuo (60 torr then 1 torr Hg) at 40° C. to give an oil which was evaporated with anhydrous pyridine (50 ml) This oil was further dried in vacuo (1 torr Hg) at 20° C. in the presence of phosphorous pentoxide overnight to give $N^6$- Benzoyl 9-(2'-fluoro-b-D-ribofuranosyl)adenine as a yellow foam (1.08 g, 100%) which contained minor impurities.

G. $N^6$-Benzoyl-9-[2'-fluoro-5'-O-(4,4'-dimethoxy-trityl)-β-D-ribofuranosyl]adenine $N^6$-Benzoyl-9-(2'-fluoro-b-D-ribofuranosyl)adenine (1.08 g, 2.89 mmol) which contained minor impurities was dissolved in anhydrous pyridine (20 ml) under an argon atmosphere, and dry triethylamine (0.52 ml, 3.76 mmol) was added followed by addition of 4,4'-dimethoxy-trityl chloride (1.13 g, 3.32 mmol). After 4 hours of stirring at 20° C. the reaction mixture was transferred to a separatory funnel and diethyl ether (40 ml) was added to give a white suspension. This mixture was washed with water three times (3×10 ml), the organic phase was separated and dried over magnesium sulfate. Triethylamine (1 ml) was added to the solution and the solvent was evaporated in vacuo (60 torr Hg) at 20° C. to give an oil which was evaporated with toluene (20 ml) containing triethylamine (1 ml). This crude product was purified by column chromatography using silica and ethylacetate-triethylamine (99:1, v/v) followed by ethyl acetate-methanol-triethylamine (80:19:1) to give the product in two fractions. The fractions were evaporated in vacuo (60 torr then 1 torr Hg) at 20° C. to give a foam which was further dried in vacuo (1 torr Hg) at 20° C. in the presence of sodium hydroxide to give $N^6$-Benzoyl-9-[2'-fluoro-5'-O-(4,4'-dimethoxytrityl)-β-D-ribofuranosyl]adenine as a foam (1.02 g, 52%).

H. $N^6$-Benzoyl-[2'-fluoro-5'-O-(4,4'-dimethoxy trityl)] adenosine-3'-O-N,N-diisopropyl-β-cyanoethyl phosphoramidite N⁶-Benzoyl-9-[2'-fluoro-5'-O-(4,4'-dimethoxy-trityl)-β-D-ribofuranosyl]adenine (1.26 g, 1.89 mmol) was dissolved in anhydrous dichloromethane (13 ml) under an argon atmosphere, diisopropylethylamine (0.82 ml, 4.66 mmol) was added, and the reaction mixture was cooled to ice temperature. Chloro(diisopropylamino)-β-cyanoethoxyphosphine (0.88 ml, 4.03 mmol) was added to the reaction mixture which was allowed to warm to 20° C. and stirred for 3 hours. Ethylacetate (80 ml) and triethylamine (1 ml) were added and this solution was washed with brine solution three times (3×25 ml). The organic phase was separated and dried over magnesium sulfate. After filtration of the solids the solvent was evaporated in vacuo at 20° C. to give an oil which was purified by column chromatography using silica and hexane-ethyl acetate-triethyl-amine (50:49:1) as eluent. Evaporation of the fractions in vacuo at 20° C. gave a foam which was evaporated with anhydrous pyridine (20 ml) in vacuo (1 torr) at 26° C. and further dried in vacuo (1 torr Hg) at 20° C. in the presence of sodium hydroxide for 24 h to give N⁶-Benzoyl-[2'-deoxy-2'-fluoro-5'-O-(4,4'-dimethoxytrityl)] adenosine- 3'-O-(N,N-diisopropyl-β-cyanoethylphosphoramidite as a foam (1.05 g, 63%).

I. 2'-Deoxy-2'-fluoro-5'-O-(4,4'-dimethoxytrityl)-uridine-3'-O-(N,N-diisopropyl-β-cyanoethyl phosphoramidite).

2,2'-Cyclouridine is treated with a solution of 70% hydrogen fluoride/pyridine in dioxane at 120° C. for ten hours to provide after solvent removal a 75% yield of 2'-deoxy-2'-fluorouridine. The 5'-DMT and 3'-cyanoethoxydiisopropylphos-phoramidite derivitized nucleoside is obtained by standard literature procedures, M. J. Gait, ed., *Oligonucleotide Synthesis. A Practical Approach*, (IRL Press, Washington, D.C., 1984) or through the procedure of Example 25A.

J. 2'-Deoxy-2'-fluoro-5'-O-(4,4'-dimethoxytrityl)-cytidine-3'-O-(N,N-diisopropyl-β-cyanoethyl phosphoramidite)

2'-Deoxy-2'-fluorouridine is converted to the corresponding cytidine analog. The 5'-O-(4,4'-dimethoxy-trityl)-3'-O-(N,N-diisopropyl-β-cyanoethylphosphoramidite) can be prepared in accordance with Example 25A.

K. 2'-Deoxy-2'-fluoro-5'-O-(4,4'-dimethoxytrityl)-guanosine -3'-O-(N,N-diisopropyl-β-cyanoethyl phosphoramidite)

2'-Deoxy-2'-fluoro guanosine was prepared according to the procedure of M. Ikehara and J. Imura, *Chemical and Pharmaceutical Bulletin* 29:1034–1038 and 3281–3285 (1981). This material was converted to the 5'-DMT-3'-phosphoramidite as described in Example 25A.

L. Preparation of 2'-Deoxy-2'-fluoro Modified Phosphorothioates Oligonucleotides 2'-Deoxy-2'-substituted 5'-DMT nucleoside 3'-phosphoramidites prepared as described in Example 25 were inserted into sequence-specific oligonucleotide phosphorothioates as described by S. Beaucage et al., *Journal of American Chemical Society* 112:1253–1255 (1990) and B. S. Sproat, et al., *Nucleic Acids Research* 17:3373–3386 (1989).

---

What is claimed is:

1. A method of treating a hyperproliferative condition associated with expression of human protein kinase C comprising administering an antisense oligonucleotide up to 50 nucleotide units in length which specifically binds mRNA encoding human protein kinase C, wherein said antisense oligonucleotide comprises a nucleotide sequence selected from the group consisting of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 67, 74, 75, 87, 93, 106, 107, 109, 110, 113, 115, 116, 117, 118, and 121, whereby expression of human protein kinase C is inhibited and said hyperproliferative condition is ameliorated.

2. The method of claim 1 wherein said hyperproliferative condition is cancer.

3. The method of claim 2 wherein said hyperproliferative condition is colorectal cancer, breast cancer, bladder cancer, lung cancer or brain cancer.

4. The method of claim 3 wherein said brain cancer is glioblastoma multiforme.

5. The method of claim 1 wherein at least one of the intersugar linkage between nucleotide units of the antisense oligonucleotide is a phosphorothioate.

6. The method of claim 1 wherein at least one of the nucleotides of the antisense oligonucleotide comprises a modification on the 2' position of the sugar.

7. The method of claim 6 wherein the modification is a 2'-O-alkyl or 2'-fluoro modification.

8. The method of claim 1 wherein the antisense oligonucleotide is a chimeric antisense oligonucleotide.

9. The method of claim 8 wherein the antisense oligonucleotide comprises a deoxy region flanked by regions of nucleotide units having 2'-O-alkyl or 2'-fluoro modifications.

10. The method of claim 1 wherein said antisense oligonucleotide is in a pharmaceutically acceptable carrier or diluent.

11. The method of claim 10 wherein said carrier or duluent comprises a cationic lipid.

12. The method of claim 1 wherein said antisense oligonucleotide comprises SEQ ID NO: 1, 2, 3, 4, 5, 6, 7, 8, 9, 10, 11, 12, 13, 14, 15, 16, 17, 18, 19, 20, 52 or 53.

13. The method of claim 1 wherein said antisense oligonucleotide comprises SEQ ID NO: 21, 22, 23, 24, 25, 26, 27, 28, 29, 30, 31, 32, 33 or 34.

14. The method of claim 1 wherein said antisense oligonucleotide comprises SEQ ID NO: 35, 36, 37, 38 or 39.

15. The method of claim 1 wherein said antisense oligonucleotide comprises SEQ ID NO: 40, 41, 42, 43, 44, 45, 46, 47, 48, 49, 50, 51, 54, 55, 56, 57, 58, 59, 60, 61 or 62.

16. The method of claim 1 wherein said antisense oligonucleotide comprises SEQ ID NO: 67, 74 or 75.

17. The method of claim 1 wherein said antisense oligonucleotide comprises SEQ ID NO: 87 or 93.

18. The method of claim 1 wherein said antisense oligonucleotide comprises SEQ ID NO: 106, 107, 109, 110, 113, 115, 116, 117, 118 or 121.

19. A method of treating a hyperproliferative condition associated with human protein kinase C comprising administering an antisense oligonucleotide up to 50 nucleotide units in length and comprising SEQ ID NO:2, 3, or 5, whereby expression of human protein kinase C is inhibited and said hyperproliferative condition is ameliorated.

20. A method of treating a hyperproliferative condition associated with expression of human protein kinase C comprising administering an antisense oligonucleotide which specifically binds mRNA encoding human protein kinase C, wherein said antisense oligonucleotide consists of a nucleotide sequence selected from the group consisting of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 67, 74, 75, 87, 93, 106, 107, 109, 110, 113, 115, 116, 117, 118, and 121, whereby expression of human protein kinase C is inhibited and said hyperproliferative condition is ameliorated.

21. The method of claim 20 wherein said hyperproliferative condition is cancer.

22. The method of claim 21 wherein said hyperproliferative condition is colorectal cancer, breast cancer, bladder cancer, lung cancer or brain cancer.

23. The method of claim 22 wherein said brain cancer is glioblastoma multiforme.

24. The method of claim 20 wherein at least one of the intersugar linkages between nucleotide units of antisense oligonucleotide is a phosphorothioate.

25. The method of claim 20 wherein at least one of the nucleotides of the antisense oligonucleotide comprises a modification on the 2' position of the sugar.

26. The method of claim 25 wherein the modification is a 2'-O-alkyl or 2'-fluoro modification.

27. The method of claim 20 wherein the antisense oligonucleotide is a chimeric oligonucleotide.

28. The method of claim 27 wherein the antisense oligonucleotide comprises a deoxy region flanked by regions of nucleotide units having 2'-O-alkyl or 2'-fluoro modifications.

29. The method of claim 20 wherein said antisense oligonucleotide is in a pharmaceutically acceptable carrier or diluent.

30. The method of claim 29 wherein said carrier or diluent comprises a cationic lipid.

31. The method of claim 20 wherein said antisense oligonucleotide consists of SEQ ID NO:1, 2, 3, 4, 5, 6, 7, 8, 9, 10, 11, 12, 13, 14, 15, 16, 17, 18, 19, 20, 52 or 53.

32. The method of claim 20 wherein said antisense oligonucleotide consists of SEQ ID NO:21, 22, 23, 24, 25, 26, 27, 28, 29, 30, 31, 32, 33 or 34.

33. The method of claim 20 wherein said antisense oligonucleotide consists of SEQ ID NO:35, 36, 37, 38 or 39.

34. The method of claim 20 wherein said antisense oligonucleotide consists of SEQ ID NO:40, 41, 42, 43, 44, 45, 46, 47, 48, 49, 50, 51, 54, 55, 56, 57, 58, 59, 60, 61 or 62.

35. The method of claim 20 wherein said antisense oligonucleotide consists of SEQ ID NO:67, 74 or 75.

36. The method of claim 20 wherein said antisense oligonucleotide consists of SEQ ID NO:87 or 93.

37. The method of claim 20 wherein said antisense oligonucleotide consists of SEQ ID NO:106, 107, 109, 110, 113, 115, 116, 117, 118 or 121.

38. A method of treating a hyperproliferative condition associated with human protein kinase C comprising administering an antisense oligonucleotide consisting of SEQ ID NO:2, 3, or 5, whereby expression of human protein kinase C is inhibited and said hyperproliferative condition is ameliorated.

39. A method of treating a hyperproliferative condition associated with expression of human protein kinase C comprising administering an antisense oligonucleotide up to 50 nucleotide units in length which specifically binds mRNA encoding human protein kinase C, wherein said oligonucleotide comprises SEQ ID NO:2, whereby expression of human protein kinase C is inhibited and said hyperproliferative condition is ameliorated.

40. A method of treating a hyperproliferative condition associated with expression of human protein kinase C comprising administering an antisense oligonucleotide up to 50 nucleotide units in length which specifically binds mRNA encoding human protein kinase C, wherein said oligonucleotide comprises SEQ ID NO:3, whereby expression of human protein kinase C is inhibited and said hyperproliferative condition is ameliorated.

41. A method of treating a hyperproliferative condition associated with expression of human protein kinase C comprising administering an antisense oligonucleotide up to 50 nucleotide units in length which specifically binds mRNA encoding human protein kinase C, wherein said oligonucleotide comprises SEQ ID NO:5, whereby expression of human protein kinase C is inhibited and said hyperproliferative condition is ameliorated.

* * * * *

UNITED STATES PATENT AND TRADEMARK OFFICE
CERTIFICATE OF CORRECTION

PATENT NO. : 5,885,970
DATED : March 23, 1999
INVENTOR(S) : Bennett and Dean

It is certified that error appears in the above-identified patent and that said Letters Patent is hereby corrected as shown below:

Col. 3, line 18, please delete "PKC-A" and insert therefor --PKC-α--;
Col. 11, line 57, please delete "n(Foster" and insert therefor --(Foster--;
Col. 13, line 21, please delete "PKC-αprotein" and insert therefor --PKC-α protein--;
Col. 13, line 32, please delete "109" and substitute therefor --10%--;
Col. 13, line 37, please delete "μM" and insert therefor --μ1--;
Col. 13, line 60, please delete "PKC-β" and insert therefor --PKC-α--;
Col. 14, line 1, please delete "PKC-β" and insert therefor --PKC-α--;
Col. 17, line 54, in Table 8 heading, please delete "2'-C" and
insert therefor --2'-O--;
Col. 23, line 55, please delete "how" and insert therefor --now--;
Col. 25, line 26, please delete "300°" and insert therefor --30°--.

Signed and Sealed this

Eighteenth Day of April, 2000

Attest:

Q. TODD DICKINSON

*Attesting Officer*   *Director of Patents and Trademarks*